(12) United States Patent
Greenhalgh et al.

(10) Patent No.: US 12,740,871 B2
(45) Date of Patent: Sep. 22, 2026

(54) METHOD AND CONTAINER FOR DELIVERING BONE GRAFT MATERIAL

(71) Applicant: SurGenTec, LLC, Boca Raton, FL (US)

(72) Inventors: Travis Greenhalgh, Boca Raton, FL (US); Andrew Shoup, Boca Raton, FL (US)

(73) Assignee: SurGenTec, LLC, Boca Raton, FL (US)

( * ) Notice: Subject to any disclaimer, the term of this patent is extended or adjusted under 35 U.S.C. 154(b) by 828 days.

(21) Appl. No.: 16/668,609

(22) Filed: Oct. 30, 2019

(65) Prior Publication Data

US 2020/0129309 A1 Apr. 30, 2020

Related U.S. Application Data

(60) Provisional application No. 62/752,867, filed on Oct. 30, 2018.

(51) Int. Cl.
*A61F 2/46* (2006.01)
*A61M 5/31* (2006.01)

(52) U.S. Cl.
CPC .......... *A61F 2/4601* (2013.01); *A61F 2/4644* (2013.01); *A61M 5/31* (2013.01);
(Continued)

(58) Field of Classification Search
CPC .................. A61F 2/4601; A61F 2/4644; A61F 2002/2835; A61F 2002/2817; A61M 5/31;
(Continued)

(56) References Cited

U.S. PATENT DOCUMENTS 2,316,095 A 4/1943 Mead, Jr.
4,277,184 A 7/1981 Solomon
(Continued)

FOREIGN PATENT DOCUMENTS

CA 2656050 2/2015
CA 3054806 A1 * 9/2018 ........... A01N 1/0221
(Continued)

OTHER PUBLICATIONS

Musculoskeletal Transplant Foundation, "NovaBone Catalog", Feb. 2013. (Year: 2013).*
(Continued)

*Primary Examiner* — Scott J Medway
(74) *Attorney, Agent, or Firm* — Knobbe, Martens, Olson & Bear, LLP

(57) ABSTRACT

A method for delivering bone graft material includes removing a container housing a bone graft material from a cryopreservation environment, wherein the bone graft material includes cellular matrix. The container includes an elongate tubular body having a first opening on a first end and a second opening on the second end. The container includes a first cap covering the first opening and a second cap covering the second opening. The method includes placing the container within a bath, removing the container from the bath, removing the first cap and the second cap from the elongate tubular body, coupling the elongate tubular body to a body of a bone graft delivery device while the bone graft material is positioned within the elongate tubular body, and delivering bone graft material through the elongate tubular body to a surgical location using the bone graft delivery device.

17 Claims, 12 Drawing Sheets

(52) U.S. Cl.
CPC ............... *A61M 2005/3104* (2013.01); *A61M 2005/3106* (2013.01)

(58) Field of Classification Search
CPC ... A61M 2005/3104; A61M 2005/3106; A61P 19/02; A01N 1/02
See application file for complete search history.

(56) References Cited

U.S. PATENT DOCUMENTS 4,338,925 A 7/1982 Miller
4,801,263 A 1/1989 Clark
5,495,719 A * 3/1996 Gray, Jr. .............. A01N 1/0263 62/78
5,531,749 A 7/1996 Michelson
5,733,288 A 3/1998 Allen
5,861,176 A 1/1999 Ducheyne et al.
6,187,047 B1 2/2001 Kwan et al.
6,224,607 B1 5/2001 Michelson
6,331,312 B1 12/2001 Lee et al.
6,348,058 B1 2/2002 Melkent
6,439,439 B1 8/2002 Rickard et al.
6,676,664 B1 * 1/2004 Al-Assir ............ A61B 17/8833 606/92
6,696,073 B2 2/2004 Boyce et al.
6,767,550 B1 7/2004 Génin et al.
6,793,660 B2 9/2004 Kerr et al.
6,814,736 B2 11/2004 Reiley et al.
7,129,035 B2 * 10/2006 Goldstein ................ A01N 1/02 435/325
7,141,054 B2 11/2006 Vandewalle
7,150,879 B1 12/2006 Lee et al.
7,214,635 B2 5/2007 Gonda et al.
7,306,603 B2 12/2007 Boehm, Jr. et al.
7,513,901 B2 4/2009 Scifert et al.
7,517,539 B1 4/2009 Lee et al.
7,578,820 B2 8/2009 Moore et al.
7,718,616 B2 5/2010 Thorne
7,799,033 B2 9/2010 Assell et al.
7,811,291 B2 10/2010 Liu et al.
7,887,543 B2 2/2011 Sand et al.
7,909,833 B2 3/2011 Voellmicke
7,964,206 B2 6/2011 Suokas et al.
8,109,961 B2 2/2012 Deshmukh
8,287,915 B2 10/2012 Clineff et al.
8,303,967 B2 11/2012 Clineff et al.
8,308,805 B2 11/2012 Lynn et al.
8,460,686 B2 6/2013 Clineff et al.
8,551,525 B2 10/2013 Cook et al.
8,613,938 B2 12/2013 Akella et al.
8,623,089 B2 1/2014 Sharkey et al.
8,628,536 B2 1/2014 Walker et al.
8,696,678 B2 * 4/2014 Foster ................. A61M 35/003 606/92
8,696,679 B2 4/2014 Shadduck et al.
8,778,378 B2 7/2014 Clineff et al.
8,932,295 B1 * 1/2015 Greenhalgh ....... A61B 17/1635 606/85
8,945,137 B1 * 2/2015 Greenhalgh ....... A61B 17/1635 606/93
9,005,286 B2 4/2015 Giorno
9,119,646 B2 9/2015 Sharkey et al.
9,138,187 B2 9/2015 Sharkey et al.
9,173,694 B2 11/2015 Kleiner
9,456,830 B2 10/2016 Greenhalgh
9,655,748 B2 5/2017 Greenhalgh et al.
9,668,881 B1 * 6/2017 Greenhalgh ....... A61B 17/1635
10,123,849 B2 11/2018 Greenhalgh
10,238,507 B2 3/2019 Greenhalgh et al.
10,271,962 B2 * 4/2019 Heald ..................... A61L 27/54
10,292,747 B2 5/2019 Greenhalgh et al.
10,405,905 B2 9/2019 Greenhalgh
10,543,105 B2 1/2020 Greenhalgh
10,555,374 B2 * 2/2020 Schryver ................. A47J 36/24
10,687,828 B2 6/2020 Greenhalgh et al.
11,116,647 B2 9/2021 Greenhalgh et al.
11,497,549 B2 11/2022 Greenhalgh
11,583,416 B2 2/2023 Greenhalgh
12,144,745 B2 11/2024 Greenhalgh
2002/0128724 A1 * 9/2002 Ollerenshaw ....... A61L 27/3691 623/23.72
2002/0155167 A1 10/2002 Lee et al.
2003/0049328 A1 3/2003 Dalal et al.
2003/0049329 A1 3/2003 Lee et al.
2003/0055512 A1 3/2003 Genin et al.
2003/0129748 A1 7/2003 Flake et al.
2003/0158602 A1 8/2003 Ting
2003/0165482 A1 * 9/2003 Rolland .............. A61L 27/3804 424/93.21
2003/0216777 A1 11/2003 Tien et al.
2004/0024409 A1 2/2004 Sand et al.
2004/0071668 A1 4/2004 Bays et al.
2004/0133211 A1 7/2004 Raskin et al.
2004/0193170 A1 * 9/2004 Kemppainen ......... A61F 2/4601 606/92
2004/0215201 A1 10/2004 Lieberman
2005/0098915 A1 5/2005 Long et al.
2005/0107800 A1 5/2005 Frankel et al.
2005/0137604 A1 6/2005 Assell et al.
2005/0142164 A1 6/2005 Lindholm et al.
2005/0171549 A1 8/2005 Boehm, Jr. et al.
2005/0203523 A1 9/2005 Wenstrom, Jr. et al.
2006/0025861 A1 2/2006 McKay
2006/0293687 A1 12/2006 Bogert
2007/0005072 A1 1/2007 Castillo et al.
2007/0016163 A1 1/2007 Santini et al.
2007/0026030 A1 2/2007 Gill et al.
2007/0026069 A1 2/2007 Shastri et al.
2007/0027230 A1 * 2/2007 Beyar .................. A61L 24/043 523/117
2007/0032794 A1 2/2007 Weber
2007/0040478 A1 2/2007 Tofail et al.
2007/0043376 A1 2/2007 Leatherbury et al.
2007/0190102 A1 8/2007 Luo
2007/0224245 A1 9/2007 Ameer et al.
2007/0233131 A1 10/2007 Song
2007/0276397 A1 11/2007 Pacheco
2007/0289998 A1 12/2007 Keller
2008/0033572 A1 2/2008 D'Antonio et al.
2008/0065082 A1 3/2008 Chang et al.
2008/0071284 A1 3/2008 Lechmann
2008/0125856 A1 5/2008 Perez-Cruet et al.
2008/0160496 A1 * 7/2008 Rzepakovsky .......... A01N 1/02 623/23.72
2008/0300684 A1 12/2008 Shelokov
2009/0024174 A1 1/2009 Stark
2009/0149707 A1 6/2009 Brannon
2009/0155332 A1 6/2009 Sherry et al.
2009/0216238 A1 8/2009 Stark
2009/0276056 A1 11/2009 Bose et al.
2009/0317447 A1 12/2009 Hsiao et al.
2009/0318925 A1 * 12/2009 Campion ............. A61F 2/4601 606/93
2009/0318982 A1 12/2009 Genin et al.
2009/0324683 A1 12/2009 Evans et al.
2009/0325775 A1 12/2009 Yeh
2010/0021518 A1 1/2010 Scifert
2010/0036381 A1 2/2010 Vanleeuwen
2010/0057087 A1 3/2010 Cha
2010/0114317 A1 5/2010 Lambrecht et al.
2010/0121459 A1 5/2010 Garigapati et al.
2010/0174286 A1 7/2010 Truckai et al.
2010/0178278 A1 7/2010 Luo et al.
2010/0179556 A1 7/2010 Scribner
2010/0204702 A1 8/2010 Lechot et al.
2010/0222750 A1 9/2010 Cheng
2010/0226959 A1 9/2010 Mckay
2010/0262146 A1 10/2010 Tulkis
2010/0297082 A1 11/2010 Guelcher et al.
2011/0071527 A1 3/2011 Nelson et al.
2011/0071536 A1 3/2011 Kleiner et al.
2011/0082424 A1 * 4/2011 Barnhouse ......... A61B 17/8827 604/125
2011/0117165 A1 5/2011 Melican et al.

(56) References Cited

U.S. PATENT DOCUMENTS

2011/0165199 A1 7/2011 Thorne
2011/0196492 A1 8/2011 Lambrecht et al.
2011/0218513 A1 9/2011 Walker et al.
2011/0237704 A1 9/2011 Guelcher et al.
2011/0243913 A1 10/2011 Antonio
2011/0276147 A1 11/2011 Cook et al.
2011/0280924 A1 11/2011 Lin et al.
2012/0053642 A1* 3/2012 Lozier .................. A61F 2/4618 606/86 R
2012/0100225 A1 4/2012 McKay
2012/0107383 A1 5/2012 McKay
2012/0253316 A1 10/2012 Oktavec et al.
2013/0090662 A1 4/2013 Hanson et al.
2013/0122057 A1 5/2013 Garigapati et al.
2013/0131683 A1 5/2013 Shah et al.
2013/0236513 A1 9/2013 Guelcher et al.
2013/0282128 A1 10/2013 McKay
2014/0039454 A1 2/2014 Sharkey
2014/0079753 A1 3/2014 Darby et al.
2014/0121781 A1 5/2014 Tunc et al.
2014/0200676 A1 7/2014 Shimko et al.
2014/0248372 A1 9/2014 Boden et al.
2014/0251438 A1 9/2014 Gettings et al.
2014/0252044 A1 9/2014 Greter et al.
2014/0255334 A1 9/2014 Raynor et al.
2014/0271779 A1 9/2014 Bagga et al.
2014/0271785 A1 9/2014 Bagga et al.
2014/0271786 A1 9/2014 Bagga et al.
2014/0271914 A1 9/2014 Wagner
2014/0277569 A1 9/2014 Lange
2014/0358188 A1 12/2014 Larson et al.
2015/0018886 A1 1/2015 Ali
2015/0054195 A1 2/2015 Greyf
2015/0071983 A1 3/2015 Bagga et al.
2015/0079146 A1 3/2015 Pomrink et al.
2015/0105748 A1* 4/2015 McBride ............. A61M 5/1452 604/218
2015/0148292 A1 5/2015 Boden et al.
2015/0165092 A1 6/2015 Kaplan et al.
2015/0283298 A1 10/2015 Kaplan et al.
2015/0283300 A1 10/2015 Pomrink et al.
2016/0082155 A1* 3/2016 Uveges .............. A61K 38/1825 424/422
2016/0228261 A1* 8/2016 Emery ............... A61B 17/8819
2017/0354515 A1 12/2017 Greenhalgh
2018/0110629 A1* 4/2018 Ewer ....................... A61F 2/442
2018/0133027 A1* 5/2018 Heald ................ A61B 17/8819
2019/0247201 A1 8/2019 Greenhalgh
2020/0046377 A1 2/2020 Woodard
2022/0241091 A1 8/2022 Greenhalgh et al.
2022/0257387 A1 8/2022 Greenhalgh
2023/0255672 A1 8/2023 Greenhalgh
2024/0024126 A1 1/2024 Greenhalgh

FOREIGN PATENT DOCUMENTS

CH 708198 12/2014
CN 1654543 8/2005
CN 101007183 8/2007
CN 101401966 4/2009
CN 101461963 6/2009
CN 101618230 1/2010
CN 104876439 9/2015
DE 10338634 3/2005
EP 0 287 584 3/1992
EP 0 891 421 1/1999
EP 0 741 785 11/1999
EP 1 018 978 7/2000
EP 1 051 205 11/2000
EP 1 121 072 8/2001
EP 1 263 353 12/2002
EP 1 311 656 5/2003
EP 1 233 794 9/2003
EP 1 344 538 9/2003
EP 1 348 453 10/2003
EP 1 359 951 11/2003
EP 1 363 551 11/2003
EP 1 365 792 12/2003
EP 1 377 236 1/2004
EP 1 383 509 1/2004
EP 1 410 810 4/2004
EP 1 140 239 7/2004
EP 0 883 410 8/2004
EP 1 194 518 9/2004
EP 1 464 345 10/2004
EP 1 250 163 12/2004
EP 1 137 448 1/2006
EP 1 085 842 3/2006
EP 1 152 777 5/2006
EP 1 624 904 1/2007
EP 1 094 851 2/2007
EP 1 753 396 2/2007
EP 0 874 601 3/2007
EP 1 778 760 5/2007
EP 1 781 319 5/2007
EP 1 804 814 7/2007
EP 1 824 530 8/2007
EP 1 909 860 4/2008
EP 1 976 459 10/2008
EP 1 981 440 10/2008
EP 1 988 940 11/2008
EP 1 996 114 12/2008
EP 2 007 317 12/2008
EP 2 010 104 1/2009
EP 2 037 973 3/2009
EP 1 210 092 4/2009
EP 2 127 689 12/2009
EP 2 131 851 12/2009
EP 1 399 199 2/2010
EP 2 182 886 5/2010
EP 2 271 378 1/2011
EP 2 272 470 1/2011
EP 1 778 306 6/2011
EP 2 358 408 8/2011
EP 2 448 607 5/2012
EP 2 456 389 5/2012
EP 2 344 081 1/2013
EP 2 542 187 1/2013
EP 2 588 154 5/2013
EP 2 600 912 6/2013
EP 2 585 124 1/2014
EP 2 678 050 1/2014
EP 2 678 052 1/2014
EP 1 677 846 8/2014
EP 2 771 041 9/2014
EP 2 793 915 10/2014
EP 1 945 132 12/2014
EP 2 823 829 1/2015
EP 2 826 495 1/2015
EP 1 528 894 6/2015
EP 2 897 560 7/2015
EP 2 512 537 8/2015
EP 2 903 657 8/2015
EP 2 904 094 8/2015
EP 2 934 394 10/2015
EP 1 986 712 12/2015
EP 1 404 346 3/2016
EP 1 638 621 3/2016
EP 1 148 847 7/2016
EP 2 605 804 3/2017
EP 2 381 970 4/2017
GB 2513599 6/2013
IN 2011DE01996 1/2013
KR 101427305 8/2014
WO WO 98/016267 4/1998
WO WO 00/027316 5/2000
WO WO 10/115138 10/2000
WO WO 05/102281 11/2005
WO WO 07/011172 1/2007
WO WO-2008032314 A2 * 3/2008 ............... A01N 1/02
WO WO 08/049242 5/2008
WO WO 08/102985 8/2008
WO WO 09/101228 8/2009

(56) References Cited

FOREIGN PATENT DOCUMENTS

| | | |
|---|---|---|
| WO | WO 11/58443 | 5/2011 |
| WO | WO 11/084731 | 7/2011 |
| WO | WO 12/134540 | 10/2012 |
| WO | WO 14/32099 | 3/2014 |
| WO | WO 14/110284 | 7/2014 |
| WO | WO 14/124496 | 8/2014 |
| WO | WO 14/147622 | 9/2014 |
| WO | WO 14/152113 | 9/2014 |
| WO | WO 14/099967 | 6/2015 |
| WO | WO 15/123733 | 8/2015 |
| WO | WO 15/123734 | 8/2015 |
| WO | WO 15/147834 | 10/2015 |

OTHER PUBLICATIONS

"Cryopreservation." Wikipedia. <https://en.wikipedia.org/wiki/Cryopreservation> (Year: 2023).*

Berkeley Advanced Biomaterials, Inc., 2014, Cem-Ostetic®, catalog, 3 pp.

Bioventus Surgical, 2017, OsteoPlus, product brochure, 5 pp.

Globus Medical Allocate product, http://www.globusmedical.com/portfolio/allocate/, 2014, 2 pp.

IFGL Bio Ceramics Ltd, Nov. 20, 2008, Bone regenerative solutions for advanced dental surgeries, 3 pp.

Kumar et al., Jun. 2013, Bone grafts in dentistry, J. Pharm Bioallied Sci, 5(Suppl1):S125-S127.

Maxigen Biotech Inc., 2010, Formagraft ® Bone Graft Substitute, product brochure, 1 p.

Medtronic, 2005, Mastergraft ®, product brochure, 12 pp.

RTI Surgical, Inc., 2017 NanOss® Loaded Advanced Bone Graft Substitute, product brochure, 3 pp.

Straumann AG, Maxresorb® inject, product brochure, 2 pp.

Stryker Corporation 1998, Vitoss Bone Graft Substitute, product brochure, 2 pp.

Trans1 Pylon, https://vimeo/com/318566244, site visted Feb. 8, 2021.

Zimmer Biomet, 2017, CopiOs® Bone Void Filler, product brochure, 7 pp.

* cited by examiner

METHOD AND CONTAINER FOR DELIVERING BONE GRAFT MATERIAL

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57. The present application claims the priority benefit of U.S. Provisional Application No. 62/752,867, filed Oct. 30, 2018, the entirety of which is hereby incorporated by reference herein.

BACKGROUND

Field

The present application relates to orthopedic surgery in general, and more particularly, to bone graft delivery systems and methods.

Description of the Related Art

In a bone grafting procedure, a surgeon places bone or a bone substitute into an area in a patient's body to provide a type of scaffold for bone growth and repair. Bone grafts can be used to help treat various orthopedic problems, for example, to fuse a joint or repair a fracture. Bone graft material can be, for example, autogenous (harvested from the patient's own body), allogeneic (harvested from another person, usually a cadaver), or synthetic. Many bone grafting procedures are performed via open surgery implantation. However, these procedures can also be performed minimally invasively, for example, by using a needle to inject the bone graft material into the target location without requiring a surgical incision.

SUMMARY

In some embodiments, a method for delivering bone graft material to a surgical location is provided. The method includes removing a container housing a bone graft material from a cryopreservation environment, wherein the bone graft material comprises cellular matrix. The container includes an elongate tubular body having a first opening on a first end and a second opening on the second end. The elongate tubular body has an outer surface area between 2258 mm$^2$ and 19355 mm$^2$ and a wall thickness between 0.5 mm and 4.0 mm. The method further includes placing the container within a bath to thaw the bone graft material, removing the container from the bath, coupling the elongate tubular body to a body of a bone graft delivery device while the bone graft material is positioned within the elongate tubular body, and delivering bone graft material through the elongate tubular body to a surgical location using the bone graft delivery device.

In some embodiments, the wall thickness is between 0.75 mm and 2.0 mm. In some embodiments, the outer surface area of the elongate tubular body is between 5677 mm$^2$ and 8194 mm$^2$. In some embodiments, removing the container from the bath includes removing the container from the bath after a temperature of the bone graft material within the container is above 20° C. In some embodiments, removing the container from the bath includes removing the container from the bath after a temperature of the bone graft material within the container is between 1° C. and 42° C. In some embodiments, removing the container from the bath comprises removing the container from the bath after a temperature of the bone graft material within the container is between 37° C. and 39° C. In some embodiments, the container includes a first plug, cap, or seal covering the first opening and a second plug, cap, or seal covering the second opening. In some embodiments, the method includes removing the first plug, cap, or seal from the elongate tubular body prior to coupling the elongate tubular body to the bone graft delivery device. In some embodiments, the method includes removing the second plug, cap, or seal from the elongate tubular body prior to delivering bone graft material. In some embodiments, the bone graft delivery device is a plunger, wherein delivering bone graft material includes advancing the plunger through the elongate tubular body. In some embodiments, the bone graft delivery device includes a handle configured to removably couple to the elongate tubular body, wherein the handle includes a channel configured to align with the first opening of the elongate tubular body and receive the plunger therethrough. In some embodiments, delivering the bone graft material is performed without rinsing the bone graft material after the bone graft material is thawed.

In some embodiments, a container for storing and delivering bone graft material is provided. The container includes an elongate tubular body having a first opening on a first end and a second opening on the second end, the elongate tubular body having an outer surface area between 2258 mm$^2$ and 19355 mm$^2$ and a wall thickness between 0.5 mm and 4.0 mm. The container further includes a first cap, plug, or seal covering the first opening, a second cap, plug, or seal covering the second opening, and a bone graft material including cellular matrix within the elongate tubular body. The elongate tubular body is configured to allow the cellular matrix to thaw from a frozen state within 8 minutes when the elongate tubular body is placed in a 23° C. bath, and/or the elongate tubular body is configured to withstand at least 30 lbf in a burst test, and/or the elongate tubular body is configured to withstand bending to 45° in a forward direction, a rearward direction, a leftward direction, and a rightward direction in a bend test.

In some embodiments, the elongate tubular body is configured to allow the cellular matrix to thaw from a frozen state within 2 minutes when the elongate tubular body is placed in a 23° C. bath. In some embodiments, the wall thickness is between 0.75 mm and 2.0 mm. In some embodiments, the outer surface area of the elongate tubular body is between 5677 mm$^2$ and 8194 mm$^2$. In some embodiments, the elongate tubular body is configured to allow the cellular matrix to thaw from a frozen state to a temperature above 20° C. within 8 minutes when the elongate tubular body is placed in a 23° C. bath. In some embodiments, the elongate tubular body is configured to allow the cellular matrix to thaw from a frozen state to a temperature above 20° C. within 2 minutes when the elongate tubular body is placed in a 23° C. bath. In some embodiments, the elongate tubular body is configured to allow the cellular matrix to thaw from a frozen state to a temperature between 1° C. and 42° C. within 8 minutes when the elongate tubular body is placed in a 23° C. bath. In some embodiments, the elongate tubular body is configured to allow the cellular matrix to thaw from a frozen state to a temperature between 1° C. and 42° C. within 2 minutes when the elongate tubular body is placed in a 23° C. bath. In some embodiments, the elongate tubular body is configured to allow the cellular matrix to thaw from a frozen state to a temperature between 35° C. and 39° C. within 8 minutes when the elongate tubular body is placed in a 23° C. bath. In some embodiments, the elongate tubular body is configured to allow the cellular matrix to thaw from a frozen state to a temperature between 35° C. and 39° C. within 2 minutes when the elongate tubular body is placed in a 23° C. bath.

In some embodiments, a bone graft delivery system includes the container and a plunger configured to be advanced through the first opening of the elongate tubular body to advance the bone graft material out of the second opening of the elongate tubular body. In some embodiments, the bone graft delivery system includes a handle configured to be removably coupled to the elongate tubular body, wherein the handle includes a channel configured to align with the first opening of the elongate tubular body and receive the plunger therethrough.

In some embodiments, a method for delivering bone graft material to a surgical location includes placing a container within a bath, the container housing a bone graft material in a frozen state, wherein the bone graft material comprises cellular matrix, wherein the container comprises an elongate tubular body having a first opening on a first end and a second opening on the second end, the elongate tubular body having an outer surface area between 2258 $mm^2$ and 19355 $mm^2$ and a wall thickness between 0.5 mm and 4.0 mm, wherein placing the container within the bath thaws the bone graft material. The method also includes removing the container from the bath, coupling the elongate tubular body to a body of a bone graft delivery device while the bone graft material is positioned within the elongate tubular body, and delivering bone graft material through the elongate tubular body to a surgical location using the bone graft delivery device.

In some embodiments, the wall thickness is between 0.75 mm and 2.0 mm. In some embodiments, the outer surface area of the elongate tubular body is between 5677 $mm^2$ and 8194 $mm^2$. In some embodiments, removing the container from the bath includes removing the container from the bath after a temperature of the bone graft material within the container is above 20° C. In some embodiments, removing the container from the bath includes removing the container from the bath after a temperature of the bone graft material within the container is between 1° C. and 42° C. In some embodiments, removing the container from the bath includes removing the container from the bath after a temperature of the bone graft material within the container is between 37° C. and 39° C. In some embodiments, the container includes a first plug, cap, or seal covering the first opening and a second plug, cap, or seal covering the second opening. In some embodiments, the method includes removing the first plug, cap, or seal from the elongate tubular body prior to coupling the elongate tubular body to the bone graft delivery device. In some embodiments, the method includes removing the second plug, cap, or seal from the elongate tubular body prior to delivering bone graft material. In some embodiments, the bone graft delivery device includes a plunger, wherein delivering bone graft material includes advancing the plunger through the elongate tubular body. In some embodiments, the bone graft delivery device includes a handle configured to removably couple to the elongate tubular body, wherein the handle includes a channel configured to align with the first opening of the elongate tubular body and receive the plunger therethrough. In some embodiments, delivering the bone graft material is performed without rinsing the bone graft material after the bone graft material is thawed.

In some embodiments, a container for storing and delivering bone graft material includes an elongate tubular body having a first opening on a first end and a second opening on a second end, the elongate tubular body having an outer surface area between 2258 $mm^2$ and 19355 $mm^2$ and a wall thickness between 0.5 mm and 4.0 mm, a first cap, plug, or seal covering the first opening, a second cap, plug, or seal covering the second opening, and a bone graft material including cellular matrix within the elongate tubular body, wherein the elongate tubular body is configured to allow the cellular matrix to thaw from a frozen state within 8 minutes when the elongate tubular body is placed in a 23° C. bath.

In some embodiments, the wall thickness is between 0.75 mm and 2.0 mm. In some embodiments, the outer surface area of the elongate tubular body is between 5677 $mm^2$ and 8194 $mm^2$. In some embodiments, the elongate tubular body is configured to allow the cellular matrix to thaw from a frozen state to a temperature above 20° C. within 2 minutes when the elongate tubular body is placed in a 23° C. bath. In some embodiments, the elongate tubular body is configured to allow the cellular matrix to thaw from a frozen state to a temperature between 1° C. and 42° C. within 2 minutes when the elongate tubular body is placed in a 23° C. bath. In some embodiments, the elongate tubular body is configured to allow the cellular matrix to thaw from a frozen state to a temperature between 35° C. and 39° C. within 2 minutes when the elongate tubular body is placed in a 23° C. bath. In some embodiments, the elongate tubular body is configured to withstand at least 30 lbf in a burst test. In some embodiments, the elongate tubular body is configured to withstand bending to 45° in a forward direction, a rearward direction, a leftward direction, and a rightward direction in a bend test. In some embodiments, the cellular matrix is thawed from a frozen state when the cellular matrix is at a temperature suitable for delivery and introduction into the body. In some embodiments, a bone graft delivery system includes the container and a plunger configured to be advanced through the first opening of the elongate tubular body to advance the bone graft material out of the second opening of the elongate tubular body. In some embodiments, the bone graft delivery system includes a handle configured to be removably coupled to the elongate tubular body, wherein the handle includes a channel configured to align with the first opening of the elongate tubular body and receive the plunger therethrough.

In some embodiments, a container for storing and delivering bone graft material includes an elongate tubular body having a first opening on a first end and a second opening on a second end, the elongate tubular body having an outer surface area to volume ratio between 0.7:1 and 1.2:1 when the surface area is measured in square millimeters and the volume is measured in cubic millimeters and a wall thickness between 0.5 mm and 4.0 mm. The container also includes a first cap, plug, or seal covering the first opening, a second cap, plug, or seal covering the second opening, and a bone graft material comprising cellular matrix within the elongate tubular body, wherein the elongate tubular body is configured to allow the cellular matrix to thaw from a frozen state within 8 minutes when the elongate tubular body is placed in a 23° C. bath.

In some embodiments, a wall thickness is between 0.75 mm and 2.0 mm. In some embodiments, the elongate tubular body is configured to allow the cellular matrix to thaw from a frozen state to a temperature above 20° C. within 2 minutes when the elongate tubular body is placed in a 23° C. bath. In some embodiments, the elongate tubular body is configured to allow the cellular matrix to thaw from a frozen state to a temperature between 1° C. and 42° C. within 2 minutes when the elongate tubular body is placed in a 23° C. bath.

In some embodiments, the elongate tubular body is configured to allow the cellular matrix to thaw from a frozen state to a temperature between 35° C. and 39° C. within 2 minutes when the elongate tubular body is placed in a 23° C. bath. In some embodiments, the elongate tubular body is configured to withstand at least 30 lbf in a burst test. In some embodiments, the elongate tubular body is configured to withstand bending to 45° in a forward direction, a rearward direction, a leftward direction, and a rightward direction in a bend test. In some embodiments, a bone graft delivery system includes the container and a plunger configured to be advanced through the first opening of the elongate tubular body to advance the bone graft material out of the second opening of the elongate tubular body. In some embodiments, the system includes a handle configured to be removably coupled to the elongate tubular body, wherein the handle includes a channel configured to align with the first opening of the elongate tubular body and receive the plunger therethrough.

In some embodiments, a method of storing a bone graft material includes providing a container including an elongate tubular body, inserting a bone graft material into the container such that an effective surface area to volume ratio is 0.7:1 and 1.2:1 when the effective surface area is measured in square millimeters and the volume is measured in cubic millimeters, and freezing the bone graft material within the container.

In some embodiments, the method further includes placing the container within a 23° C. bath to thaw the bone graft material within 8 minutes. In some embodiments, placing the container within the 23° C. bath to thaw the bone graft material within 8 minutes includes placing the container within the 23° C. bath to thaw the bone graft material within 2 minutes. In some embodiments, the method further includes removing the container from the bath after a temperature of the bone graft material within the container is above 20° C. In some embodiments, the method further includes removing the container form the bath after a temperature of the bone graft material within the container is between 1° C. and 42° C. In some embodiments, removing the container form the bath comprises removing the container form the bath after a temperature of the bone graft material within the container is between 37° C. and 39° C. In some embodiments, the method further includes placing the container within a bath to thaw the bone graft material, removing the container from the bath, coupling the elongate tubular body to a body of a bone graft delivery device while the bone graft material is positioned within the elongate tubular body, and delivering bone graft material through the elongate tubular body to a surgical location using the bone graft delivery device. In some embodiments, the container includes a first opening on a first end of the elongate tubular body, a second opening on a second end of the elongate tubular body, a first plug, cap, or seal covering the first opening, and a second plug, cap, or seal covering the second opening, the method further including removing the first plug, cap, or seal from the elongate tubular body prior to coupling the elongate tubular body to the bone graft delivery device. In some embodiments, the method further includes removing the second plug, cap, or seal from the elongate tubular body prior to delivering bone graft material. In some embodiments, the bone graft delivery device includes a plunger, wherein delivering bone graft material includes advancing the plunger through the elongate tubular body. In some embodiments, the bone graft delivery device includes a handle configured to removably couple to the elongate tubular body, wherein the handle includes a channel configured to align with an opening of the elongate tubular body and receive the plunger therethrough. In some embodiments, delivering the bone graft material is performed without rinsing the bone graft material after the bone graft material is thawed.

In some embodiments, a method for thawing a bone graft material includes receiving a container including an elongate tubular body and housing a bone graft material in a frozen state, wherein an effective surface area to volume ratio is 0.7:1 and 1.2:1 when the effective surface area is measured in square millimeters and the volume is measured in cubic millimeters, and placing the container within a bath to thaw the bone graft material.

In some embodiments, the bath is at a temperature of 23° C. and placing the container within the bath to thaw the bone graft material includes placing the container within the bath to thaw the bone graft material within 8 minutes. In some embodiments, placing the container within the bath to thaw the bone graft material within 8 minutes includes placing the container within the bath to thaw the bone graft material within 2 minutes. In some embodiments, the method includes removing the container from the bath after a temperature of the bone graft material within the container is above 20° C. In some embodiments, the method includes removing the container form the bath after a temperature of the bone graft material within the container is between 1° C. and 42° C. In some embodiments, removing the container form the bath includes removing the container form the bath after a temperature of the bone graft material within the container is between 37° C. and 39° C. In some embodiments, the method includes removing the container from the bath, coupling the elongate tubular body to a body of a bone graft delivery device while the bone graft material is positioned within the elongate tubular body, and delivering bone graft material through the elongate tubular body to a surgical location using the bone graft delivery device. In some embodiments, the container includes a first opening on a first end of the elongate tubular body, a second opening on a second end of the elongate tubular body, a first plug, cap, or seal covering the first opening, and a second plug, cap, or seal covering the second opening, the method further including removing the first plug, cap, or seal from the elongate tubular body prior to coupling the elongate tubular body to the bone graft delivery device. In some embodiments, the method further includes removing the second plug, cap, or seal from the elongate tubular body prior to delivering bone graft material. In some embodiments, the bone graft delivery device includes a plunger, wherein delivering bone graft material comprises advancing the plunger through the elongate tubular body. In some embodiments, the bone graft delivery device includes a handle configured to removably couple to the elongate tubular body, wherein the handle includes a channel configured to align with an opening of the elongate tubular body and receive the plunger therethrough. In some embodiments, delivering the bone graft material is performed without rinsing the bone graft material after the bone graft material is thawed.

DETAILED DESCRIPTION

Several types of bone graft material include live cells. Bone graft materials with live cells are frequently stored in a frozen or cryopreserved state prior to delivery to a target location of a user. Many of these bone graft materials must be frozen prior to use to maintain the integrity of the live cells. If the live cells are not cryopreserved or used within a certain amount of time, the cells begin to die off.

Traditionally, prior to delivery to a patient, bone graft materials with live cells are stored in containers that are stored in freezers and transported with dry ice to maintain temperatures suitable for maintaining cell viability. These temperatures may be between −50° C. and −110° C. The bone graft material can be cryopreserved prior to transport to a medical facility, during transport to a medical facility, and after receipt at the medical facility prior to implantation in a patient.

Figure 1:
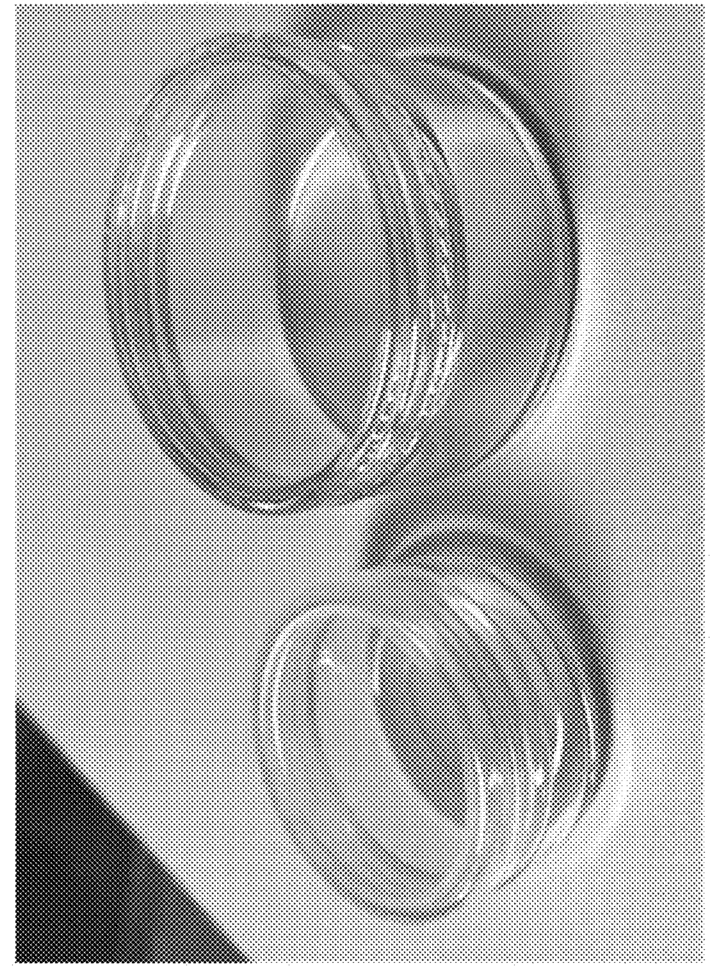
FIG. 1 illustrates an example of a traditional container for storing bone graft material.

Examples of traditional containers for storing bone graft materials are illustrated in FIG. 1.

At the beginning of a bone graft delivery procedure, the container housing the bone graft material having live cells is thawed in the operating room or space of use. With traditional bone graft containers, such as those shown in FIG. 1, thawing properly can be time-consuming and non-uniform. A standard vial is round and wide. The average width (outer diameter) is 40 mm and can hold from 1-15 cc of bone graft material. It can take a significant amount of time to thaw the bone graft material to the core and prepare the bone graft material for use. Medical staff typically have to thaw traditional containers for a minimum of 10 minutes or more.

In traditional bone graft procedures, when thawing/defrosting to room temperature, the operating room staff may place the bone graft containers in hot saline/water or warm saline/water to thaw or defrost the bone graft material within the containers. After thawing, the bone graft material is traditionally loaded into other devices such as syringes, funnels, or other suitable means to deliver the bone graft material. In some traditional procedures, when the bone graft material is used for spine and orthopedic surgery, a user may load a funnel with a push rod to tamp the bone graft material into the desired location. These procedures can be time consuming and dangerous due to the extended loading/delivery time and placement of the funnel near delicate anatomical structures or nerves. Further, the removal of the bone graft from the bone graft container and movement between the container and devices can increase the risk of contamination.

In certain embodiments, a method for delivering bone graft material to a surgical location is provided. The method includes removing a container housing a bone graft material from a cryopreservation environment, wherein the bone graft material includes cellular matrix. The container includes an elongate tubular body having a first opening on a first end and a second opening on the second end. The elongate tubular body has an outer surface area between 2,258 $mm^2$ (3.5 $in^2$) and 19,355 $mm^2$ (30 $in^2$) and a wall thickness between 0.5 mm and 4.0 mm. The container includes a first cap covering the first opening and a second cap covering the second opening. The method includes placing the container within a bath to thaw the bone graft material, removing the container from the bath, removing the first cap and the second cap from the elongate tubular body, coupling the elongate tubular body to a body of a bone graft delivery device while the bone graft material is positioned within the elongate tubular body, and delivering bone graft material through the elongate tubular body to a surgical location using the bone graft delivery device. In certain embodiments, the wall thickness is between 0.75 mm and 2.0 mm. In certain embodiments, the outer surface area of the elongate tubular body is between 5,677 $mm^2$ (8.8 $in^2$) and 8,194 $mm^2$ (12.7 $in^2$). In certain embodiments, removing the container from the bath includes removing the container from the bath after a temperature of the bone graft material within the container is above 20° C.

In certain embodiments, a container for storing and delivering bone graft material is provided. The container includes an elongate tubular body having a first opening on a first end and a second opening on the second end, the elongate tubular body having an outer surface area between 2,258 $mm^2$ (3.5 $in^2$) and 19,355 $mm^2$ (30 $in^2$) and a wall thickness between 0.5 mm and 4.0 mm. The container includes a first cap covering the first opening, a second cap covering the second opening, and a bone graft material including cellular matrix within the elongate tubular body. The elongate tubular body is configured to allow the cellular matrix to thaw from a frozen state within 8 minutes when the elongate tubular body is placed in a 23° C. bath, and/or the elongate tubular body is configured to withstand at least 30 lbf in a burst test, and/or the elongate tubular body is configured to withstand bending to 45° in a forward direction, a rearward direction, a leftward direction, and a rightward direction in a bend test. In certain embodiments, the wall thickness is between 0.75 mm and 2.0 mm. In certain embodiments, the surface area of the elongate tubular body is between 5,677 $mm^2$ (8.8 $in^2$) and 8,194 $mm^2$ (12.7 $in^2$).

In some embodiments, the elongate tubular body is configured to allow the cellular matrix to thaw from a frozen state within 2 minutes when the elongate tubular body is placed in a 23° C. bath. In some embodiments, the elongate tubular body is configured to allow the cellular matrix to thaw from a frozen state to a temperature above 20° C.

within 8 minutes when the elongate tubular body is placed in a 23° C. bath. In some embodiments, the elongate tubular body is configured to allow the cellular matrix to thaw from a frozen state to a temperature above 20° C. within 2 minutes when the elongate tubular body is placed in a 23° C. bath. In some embodiments, the elongate tubular body is configured to allow the cellular matrix to thaw from a frozen state to a temperature between 1° C. and 42° C. within 8 minutes when the elongate tubular body is placed in a 23° C. bath. In some embodiments, the elongate tubular body is configured to allow the cellular matrix to thaw from a frozen state to a temperature between 1° C. and 42° C. within 2 minutes when the elongate tubular body is placed in a 23° C. bath. In some embodiments, the elongate tubular body is configured to allow the cellular matrix to thaw from a frozen state to a temperature between 35° C. and 39° C. within 8 minutes when the elongate tubular body is placed in a 23° C. bath. In some embodiments, the elongate tubular body is configured to allow the cellular matrix to thaw from a frozen state to a temperature between 35° C. and 39° C. within 2 minutes when the elongate tubular body is placed in a 23° C. bath.

In certain embodiments, methods for delivering bone graft material to a surgical location are provided. In certain embodiments, a method for delivering bone graft material to a surgical location can include delivering bone graft material through a bone graft delivery system or a bone graft delivery device. Examples of such bone graft delivery systems and bone graft delivery devices are described in U.S. Pat. Nos. 8,932,295, 9,456,830, 8,945,137, 9,668,881, 9,655,748, U.S. patent application Ser. No. 16/384,826, U.S. patent application Ser. No. 15/614,435, U.S. patent application Ser. No. 15/902,851, U.S. patent application Ser. No. 15/495,794, U.S. patent application Ser. No. 15/902,872, and U.S. patent application Ser. No. 14/992,954, each of which is hereby incorporated by reference in its entirety.

In certain embodiments, a method for delivering bone graft material to a surgical location can include positioning a bone graft delivery device adjacent to a surgical location. In certain embodiments, the surgical location is a portion of the patient's spine, and the bone graft delivery device is positioned adjacent to the spine.

In certain embodiments, a method for delivering bone graft material to a surgical location can include loading a bone graft delivery device with bone graft material. In certain embodiments, the bone graft material can include synthetic, autologous, viable bone matrix, cellular matrix, stem cell, demineralized bone matrix (DBM), cortical fibers, demineralized cortical fibers, cadaveric, and/or any other available bone graft material. In some embodiments, the bone graft materials can include one or more of hydroxyapatite (HA), tricalcium phosphate (TCP), and bioglass.

In certain embodiments, the methods described herein can include freezing or cryopreserving the bone graft material. For example, in certain embodiments, the methods described herein can include freezing or cryopreserving viable bone matrix, cellular matrix, stem cells, or other products containing live cells. In certain embodiments, the methods described herein can include freezing or cryopreserving one or more allografts that do not include live cells. For example, in certain embodiments, the methods described herein can include freezing or cryopreserving allograft containing cancellous and/or cortical bone.

In certain embodiments, the bone graft material can be stored in a container made of made of polymers, metal, glass or any other materials that can resist cracking, breaking or degrading in the low storage temperatures. In certain embodiments, the container can be a tube. In certain embodiments, the container can include a plurality of markings to indicate an amount of bone graft material within the container.

In certain embodiments, the container can be attached to a bone graft delivery device or bone graft delivery system for delivery of the bone graft material to the surgical location. In certain embodiments, the bone graft container can be attached to one of the bone graft delivery devices described in U.S. Pat. Nos. 8,932,295, 9,456,830, 8,945,137, 9,668,881, 9,655,748, U.S. patent application Ser. No. 16/384,826, U.S. patent application Ser. No. 15/614,435, U.S. patent application Ser. No. 15/902,851, U.S. patent application Ser. No. 15/495,794, U.S. patent application Ser. No. 15/902,872, or U.S. patent application Ser. No. 14/992,954. In certain embodiments, the container can be used as an elongate tube as described in any of the aforementioned patents or patent applications.

Figure 2A:
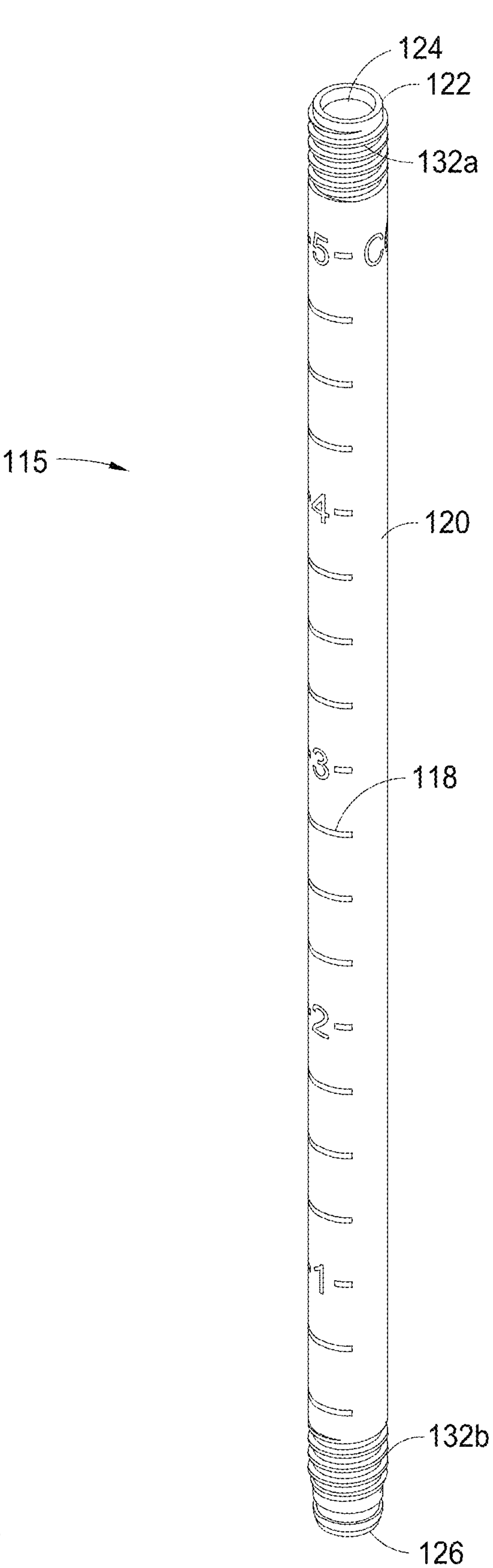
FIG. 2A illustrates a first perspective view of an embodiment of a container for storing bone graft material.
Figure 2B:
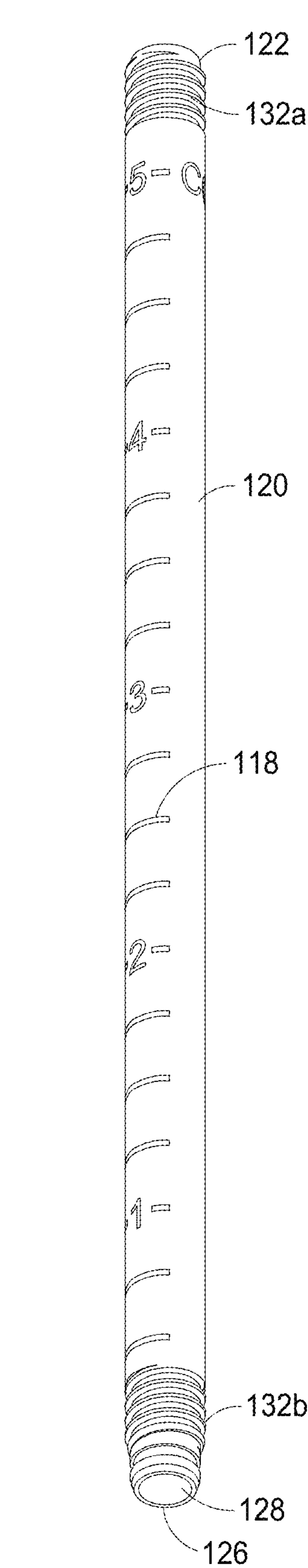
FIG. 2B illustrates a second perspective view of the container of FIG. 2A.

FIGS. 2A-B depict perspective views of an embodiment of a bone graft container 115. In certain embodiments, the bone graft container 115 can be used for the storage and cryopreservation of bone graft material.

The bone graft container 115 is generally in the form of an elongate tube. The container 115 includes an elongate tubular body 120. The elongate tubular body 120 can have a first end 122 having an opening 124 and a second end 126 having an opening 128. A lumen can extend between the opening 124 and the opening 128.

Figure 2C:
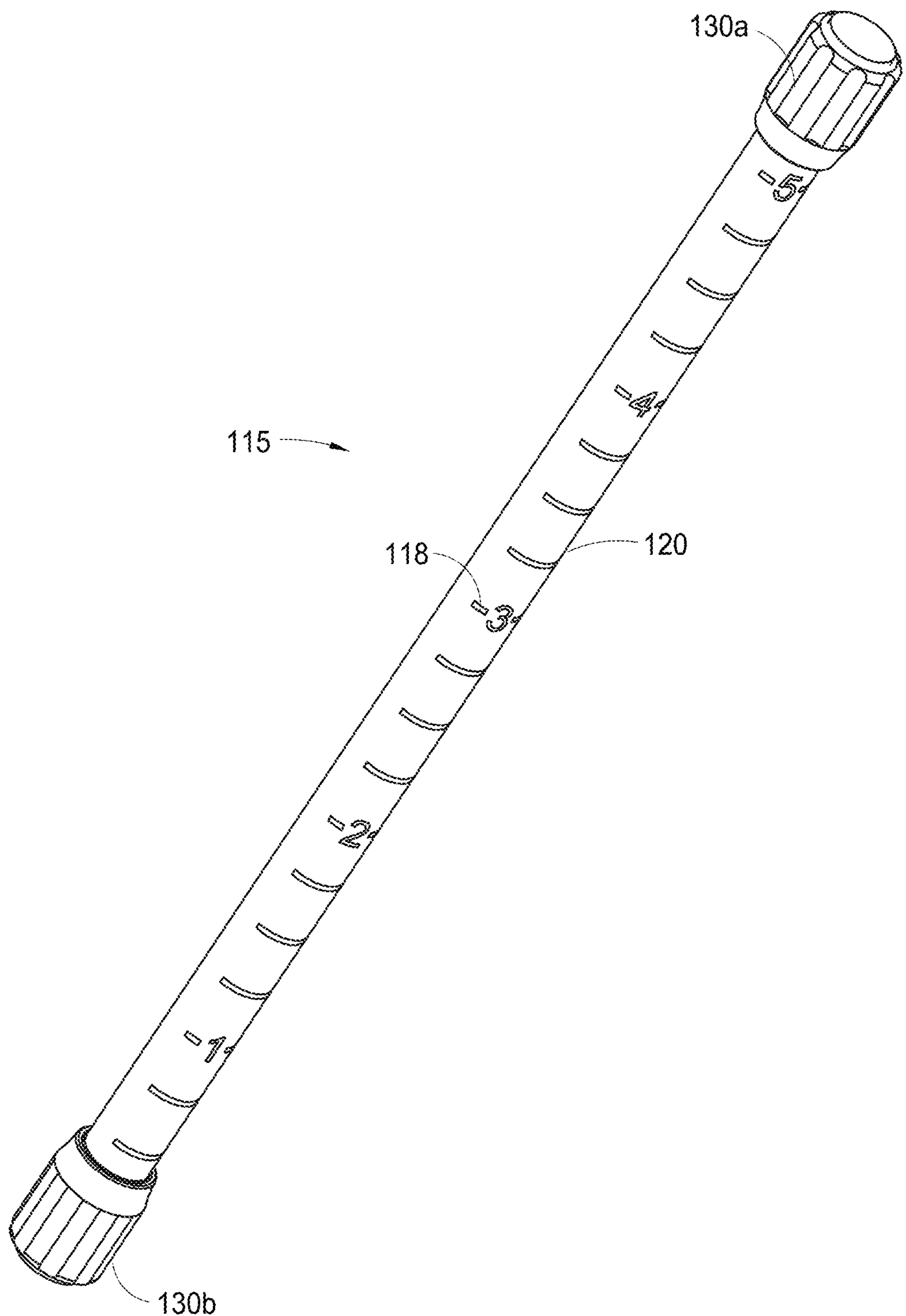
FIG. 2C illustrates a perspective view of the container of FIG. 2A coupled with a pair of caps.

In certain embodiments, the container 115 can include one or more caps configured to cover one or both of the openings 124 and 128. FIG. 2C depicts a perspective view of the container 115 including a cap 130*a* and a cap 130*b*. In certain embodiments, the cap 130*a* can cover the opening 124. In certain embodiments, the cap 130*a* can be attached to the first end 122 of the elongate tubular body via a threaded coupling, friction fit, or other suitable connection. In certain embodiments, the first end 122 can include threads 132*a*. In certain embodiments, the threads 132*a* can be external threads configured to attach to internal threads of the cap 130*a*. In certain embodiments a plug or seal can be used to cover the opening 124 instead of the cap 130*a*.

In certain embodiments, the cap 130*b* can cover the opening 128. In certain embodiments, the cap 130*b* can be attached to the second end 126 of the elongate tubular body 130*b* via a threaded coupling, friction fit, or other suitable connection. In certain embodiments, the second end 126 can include threads 132*b*. In certain embodiments, the threads 132*b* can be external threads configured to attach to internal threads of the second cap. In certain embodiments a plug or seal can be used to cover the opening 128 instead of the cap 130*b*.

Figure 2D:
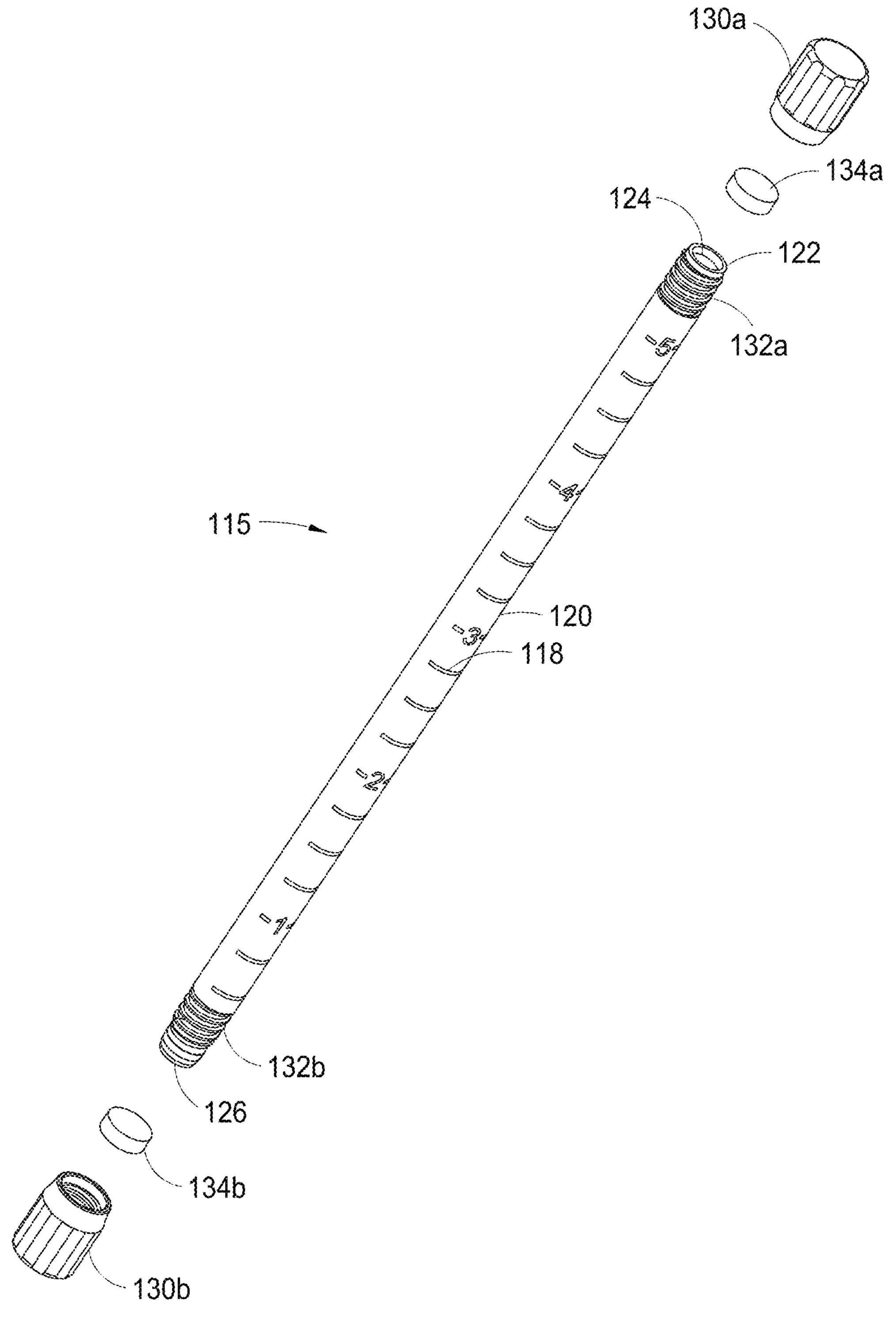
FIG. 2D illustrates an exploded view of the container and caps of FIG. 2C.
Figure 3A:
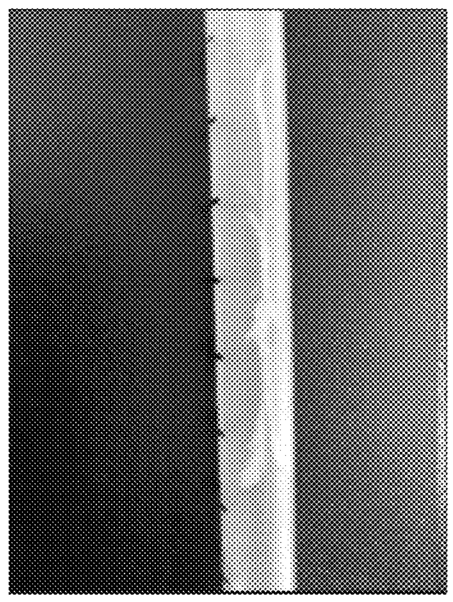
FIG. 3A illustrates an example of a container having failed a burst test.
Figure 3B:
FIG. 3B illustrates an example of a container having failed a burst test.
Figure 3C:
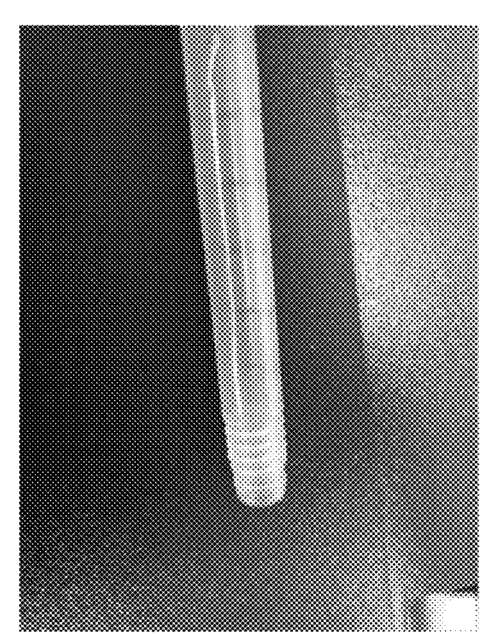
FIG. 3C illustrates an example of a container having failed a burst test.
Figure 3D:
FIG. 3D illustrates an example of a container having failed a burst test.

FIG. 2D depicts an exploded perspective view of the container 115 and caps 130*a* and 130*b*. As shown in FIG. 2D, in certain embodiments, the container 115 can include a gasket 134*a*. The gasket 134*a* can be shaped, dimensioned, or otherwise configured to form a seal around the opening 124. In certain embodiments, the gasket 134*a* can be positioned within the cap 130*a*. In certain embodiments, the gasket 134*a* can be coupled to the cap 130*a*. The gasket 134*a* can form a seal between the cap 130*a* and the end 122 of the elongate tubular body 120.

In certain embodiments, the container 115 can include a gasket 134*b*. The gasket 134B can be shaped, dimensioned, or otherwise configured to form a seal around the opening 128. In certain embodiments, the gasket 134*b* can be positioned within the cap 130*b*. In certain embodiments, the gasket 134*b* can be coupled to the cap 130*b*. The gasket 134*b* can form a seal between the cap 130*b* and the end 126 of the elongate tubular body 120.

In certain embodiments, the elongate tubular body 120 can be configured to removably receive the cap 130*a* and the cap 130*b*. The caps 130*a* and 130*b* can be placed on each end 122 and 124 of the elongate tubular body 120 when the container 115 is initially loaded with bone graft material.

In certain embodiments, the lumen of the elongate tubular body 120 can define an internal volume configured to house bone graft material. For example, the elongate tubular body can house bone 120 can house bone graft material including cellular matrix bone graft material.

In certain embodiments, the elongate tubular body 120 can have a surface area between 2,258 $mm^2$ (3.5 $in^2$) and 19,355 $mm^2$ (30 $in^2$) and a wall thickness between 0.5 mm and 4.0 mm. In certain embodiments, a wall thickness of the elongate tubular body 115 is between 0.75 mm and 2.0 mm. In certain embodiments, the surface area of the elongate tubular body 115 is between 5,677 $mm^2$ (8.8 $in^2$) and 8,194 $mm^2$ (12.7 $in^2$).

In certain embodiments, the container 115 can be used in a method of thawing the frozen or cryopreserved cellular matrix bone graft material. For example, in certain embodiments, the container 115 housing the cellular matrix bone graft material can be placed in a bath to thaw the cellular matrix bone graft material within the container 115. In certain embodiments, the elongate tubular body 120 is configured to allow the cellular matrix bone graft material within the elongate tubular body 120 to thaw from a frozen state within 2 minutes when the elongate tubular body 120 is placed in a 23° C. bath. In certain embodiments, the elongate tubular body 120 is configured to allow the cellular matrix bone graft material within the elongate tubular body 120 to thaw from a frozen state within 10 minutes, 8 minutes, 6 minutes, 4 minutes, 2 minutes, 1 minute, or any other suitable length of time when the elongate tubular body 120 is placed in a 23° C. bath. In certain embodiments, the container 115 can be thawed in a bath until the temperature of the bone graft material is between 1° C. and 42° C. In certain embodiments, cell death can occur in bone graft material at temperatures above 42° C. In certain embodiments, an optimal thawing temperature of the bone graft material can be between 35° C. and 39° C.

In some embodiments, the elongate tubular body 120 is configured to allow the cellular matrix to thaw from a frozen state to a temperature above 20° C. within 2 minutes when the elongate tubular body 120 is placed in a 23° C. bath. In some embodiments, the elongate tubular body 120 is configured to allow the cellular matrix to thaw from a frozen state to a temperature above 20° C. within 10 minutes, 8 minutes, 6 minutes, 4 minutes, 2 minutes, 1 minute, or any other suitable length of time when the elongate tubular body 120 is placed in a 23° C. bath. In some embodiments, the elongate tubular body 120 is configured to allow the cellular matrix to thaw from a frozen state to a temperature between 1° C. and 42° C. within 2 minutes when the elongate tubular body is placed in a 23° C. bath. In some embodiments, the elongate tubular body 120 is configured to allow the cellular matrix to thaw from a frozen state to a temperature between 1° C. and 42° C. within 10 minutes, 8 minutes, 6 minutes, 4 minutes, 2 minutes, 1 minute, or any other suitable length of time when the elongate tubular body 120 is placed in a 23° C. bath. In some embodiments, the elongate tubular body 120 is configured to allow the cellular matrix to thaw from a frozen state to a temperature between 35° C. and 39° C. within 2 minutes when the elongate tubular body 120 is placed in a 23° C. bath. In some embodiments, the elongate tubular body 120 is configured to allow the cellular matrix to thaw from a frozen state to a temperature between 35° C. and 39° C. within 10 minutes, 8 minutes, 6 minutes, 4 minutes, 2 minutes, 1 minute, or any other suitable length of time when the elongate tubular 120 body is placed in a 23° C. bath.

In certain embodiments, the elongate tubular body 120 is configured to withstand at least 30 lbf in a burst test. In certain embodiments, the elongate tubular body 120 is configured to withstand bending to 45° in a forward direction, a rearward direction, a leftward direction, and a rightward direction in a bend test.

In certain embodiments, the elongate tubular body 120 can be formed of polymers, metal, glass, and/or any other materials that can resist cracking, breaking, and/or degrading in low storage temperatures, for example, temperatures used for cryopreservation.

In certain embodiments, the elongate tubular body 120 can include a plurality of markings 118. The markings 118 can provide an indication of an amount of bone graft material within the container 115. In certain embodiments, the markings 118 can include one or more radiopaque markers.

In certain embodiments, after the bone graft material within the container 115 is thawed, the bone graft material can be delivered from the container 115 to a surgical location. In certain embodiments, the container 115 can be attached to a bone graft delivery device for the delivery of bone graft material to a surgical location. For example, in certain embodiments, the container 115 can be attached to a handle of a bone graft delivery device.

In certain embodiments, one of the ends 122 and 126 can be configured to couple to a bone graft delivery device. In certain embodiments, the threads 132*a* or 132*b* can be configured to couple to complementary threads of a bone graft delivery device. In certain embodiments, the other end 122 or 126 can be positioned to allow bone graft material to flow out of the elongate tubular body 120 and into a surgical location through the opening 124 or the opening 126.

In certain embodiments, the elongate tubular body 120 can be configured to receive a plunger when the elongate tubular body 120 is coupled to a bone graft delivery device. For example, the elongate tubular body 120 can be configured to receive a plunger through the opening 124 or 128 in the end 122 or 126 of the elongate tubular body 120 secured to the bone graft delivery device. In certain embodiments, the plunger can advance through the elongate tubular body to cause bone graft material to advance out of the opening 124 or 126 of the other end 122 or 126 of the elongate tubular body. In some embodiments, the plunger can include notches or teeth or any other suitable surface feature to facilitate advancement of the plunger by a drive mechanism of the bone graft delivery device. In some embodiments, the plunger can be generally smooth. In some embodiments, the plunger may be activated using mechanical, electric, pneumatic force, or any other suitable force.

Bone graft delivery systems can come in numerous configurations. In some embodiments, the container 115 can be used in conjunction with a pusher rod or plunger, which can be traversed through the elongate tubular body 115 to extend bone graft material out of the container 120. In some embodiments, a bone graft delivery system can include a spindle drive with rotating spiral plunger for driving bone graft out of the container 120. In some embodiments, the bone graft delivery system can include a ratcheting mechanism, a worm gear, a spool drive, trigger drive, or any other suitable drive for driving bone graft out of the bone graft container 120.

Figure 5:
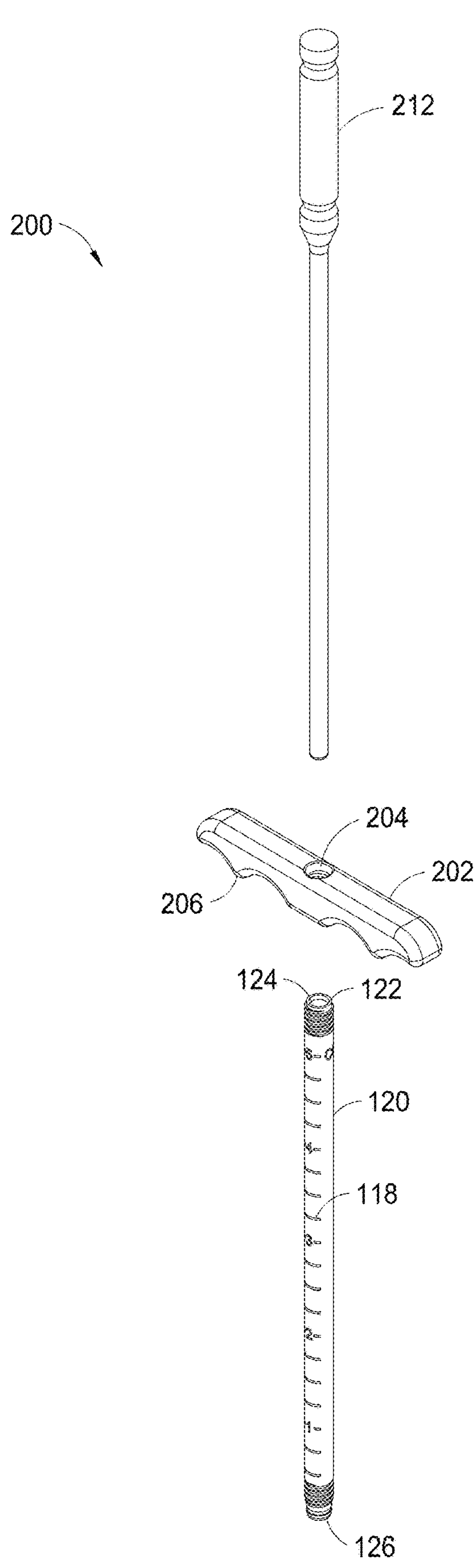
FIG. 5 illustrates an exploded perspective view of an embodiment of a bone graft delivery system including the container of FIG. 2A.
Figure 6:
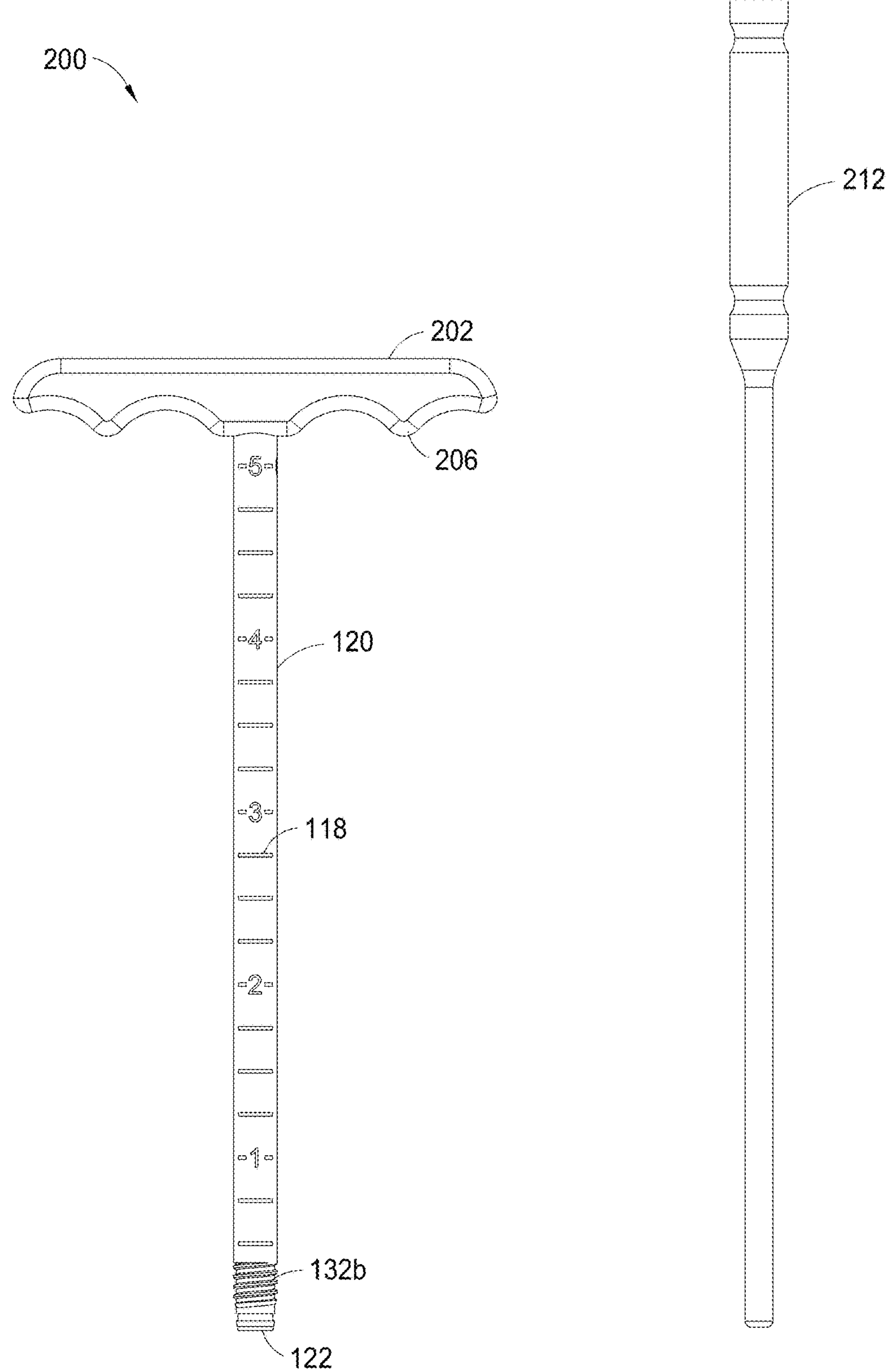
FIG. 6 illustrates an exploded front view of an embodiment of a bone graft delivery system of FIG. 5.
Figure 7:
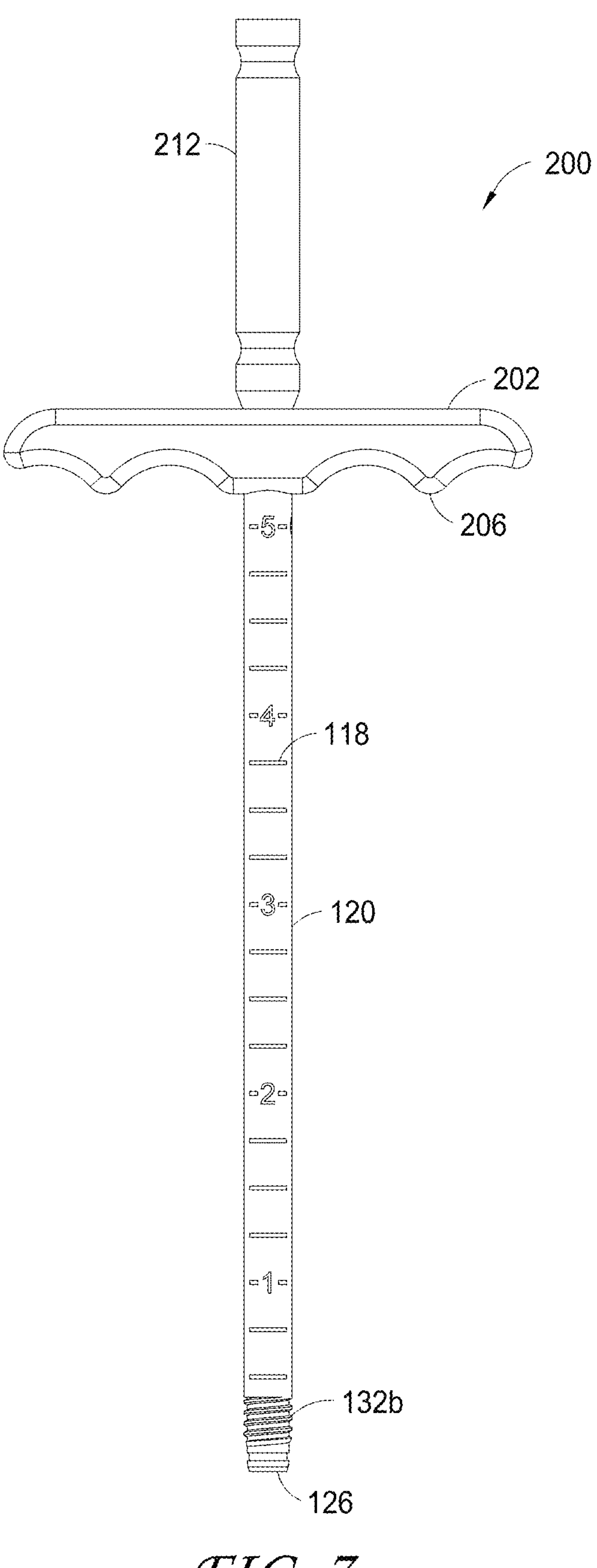
FIG. 7 illustrates a front view of the bone graft delivery system of FIG. 5.
Figure 8:
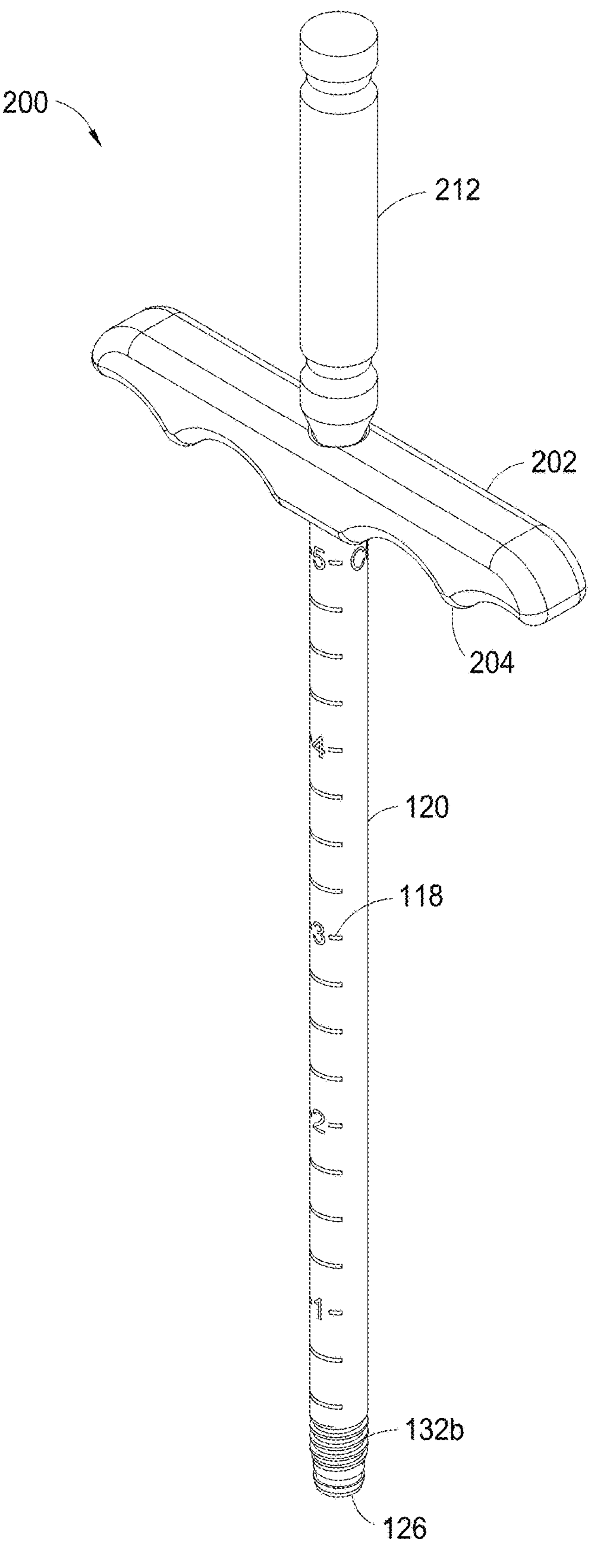
FIG. 8 illustrates a perspective view of the bone graft delivery system of FIG. 5.

FIGS. 5-8 depict an embodiment of a bone graft delivery system 200. FIG. 5 depicts an exploded perspective view of the bone graft delivery system 200. FIG. 6 depicts an exploded view of the bone graft delivery system 200. FIG. 7 depicts a front view of the bone graft delivery system 200. FIG. 8 depicts a perspective view of the bone graft delivery system 200.

In certain embodiments, the bone graft delivery system 200 can include a pushrod or plunger 212. In certain embodiments, the pushrod or plunger 212 can be used as a bone graft delivery device. In certain embodiments, the pushrod or plunger can be inserted into one of the openings 124 and 128 of one of the ends 122 and 126 of the elongate tubular body 120 to cause bone graft to flow out of the other of the openings 124 and 128.

In certain embodiments, the bone graft delivery system can include a handle 202. In certain embodiments, the handle 202 can be a bone graft delivery device or part of a bone graft delivery device. The handle 202 can be removably coupled to the elongate tubular body 120. In certain embodiments, the handle 202 can be configured to couple to one of the ends 122 and 126 of the elongate tubular body 120. For example, in certain embodiments, the handle 202 can include complementary threads configured to couple to the threads 132*a* or 132*b* of the elongate tubular body 120. In certain embodiments, the handle 202 and tubular body 120 can be coupled to form a bone graft delivery device.

In certain embodiments, the handle 202 can include a channel 204 configured to align with the opening 124 or the opening 126 when the handle 202 is coupled to the end 122 or the end 126, respectively. The channel 204 can be configured to receive the pushrod or plunger 212. In use the pushrod or plunger 212 can be inserted through the channel 204 and lumen of the elongate tubular body 120 to cause the flow of bone graft material out of the elongate tubular body 120. In certain embodiments, the plunger 212, handle 202 and elongate tubular body 120 can form a bone graft delivery device.

In certain embodiments, the handle 202 can be gripped for support and stability during use of the bone graft delivery system 200. In certain embodiments, the handle 202 can be manipulated by a user to position the elongate tubular body 120. In certain embodiments, the handle 202 can include one or more finger grips or other surface features 206 to facilitate gripping by a user.

In some embodiments, the bone graft delivery system 200 may be operated without the handle 202. In certain embodiments, the pushrod 212 may be used without the handle to extrude bone graft from the elongate tubular body 120, for example, in minimally invasive applications or for delivery to tight spaces. In certain embodiments, the pushrod 212 and the elongate tubular body 120 can act together as a bone graft delivery device.

In certain embodiments, the plunger or pushrod 212 and/or handle 202 can be packaged together with the container 115 as a kit. In other embodiments, the pushrod 212, handle 202, and/or container 115 can be provided separately.

In certain embodiments, the elongate tubular body 120 can be configured to removably receive the cap 130*a* and the cap 130*b*. The caps 130*a* and 130*b* can be placed on each end 122 and 124 of the elongate tubular body 120 when the container 115 is initially loaded with bone graft material. The caps 130*a* and 130*b* can prevent leakage of the bone graft material during storing and transport of the container 120.

In certain embodiments, the bone graft material can be cryopreserved in the container 115 at a temperature between −40° C. and −110° C. In certain embodiments, the bone graft material can be cryopreserved in the container 115 at a temperature between −35° C. and −90° C. In certain embodiments, these are the temperatures in which the cells remain viable during storage.

In certain embodiments, the container 115 can be stored in a freezer prior to shipment to a medical facility or at a medical facility prior to delivery to the patient. In certain embodiments, the container 115 can be transported in a container having dry ice to maintain temperatures for cell viability.

In certain embodiments, one or more cryopreservative agents can be used in the bone graft material. Cryopreservative agents can prevent live cells in a bone graft material from lysing or dying. In certain embodiments, these cryopreservative agents can be mixed in a container with the cells of the bone graft material prior to cryopreservation. In certain embodiments, the cryopreservative agents can be mixed with the bone graft material in the same container 115 in which the material is stored. In certain embodiments, cryopreservative agents can include one or more of DMSO, CryoNovo™, T82, pZerve, and multiple other cryomedias/cryopreservatives In certain embodiments, the bone graft material does not contain cryopreservatives or contains a minimal amount of cryopreservatives. Minimizing the amount of cryopreservatives can allow users to avoid decanting and rinsing the graft so it may be dispensed directly to surgical site. For example, in certain embodiments, the bone graft material does not contain cryopreservative agents or contains a minimal amount of cryopreservative agents so that the container 120 does not have to be emptied and/or reloaded prior to attachment to the bone graft delivery device and/or so specialized instruments for decanting are not necessary. With conventional bone graft delivery vials, a vial is defrosted for an extended period of time, rinsed or decanted, and then reloaded into a funnel or delivery device for delivery of bone graft material.

In certain embodiments, the bone graft material includes cellular allografts. Cellular allografts are processed with the extraction of cancellous and/or cortical bone or a portion of both. A ratio combination of both cancellous and cortical bone can be important for efficacy of the graft because each lends its own component for cellular growth/handling characteristics/scaffolding properties for bone growth. Cancellous bone can improve cellular growth. Cells are predominantly found in cancellous bone due to the bone marrow. Cortical bone contains BMP's (Bone morphogenic proteins) which can signal bone growth. Cortical bone also provides a scaffolding for bone growth as well as optimal handling characteristics.

In certain embodiments, bone particles in the cellular matrix may be extracted, milled, manipulated, or otherwise provide in an array of shapes and sizes. Bone particles may be shaped and/or dimensioned to improve one or more of handling, flowability, osteoconductivity and other bone growth properties.

In certain embodiments, particle sizes of cancellous particles/fibers in the bone graft material can be 1.5 mm or less. In certain embodiments, particle sizes for cortical particles/fibers in the bone graft material can be less than 12 mm. These particle sizes can allow for optimal bone growth and can allow the bone graft to flow properly through an elongate tube container, such as container 115, for graft delivery to a surgical site. Cancellous or cortical bone particles/fibers are larger than the aforementioned sizes can produce an increased risk of jamming in an elongate tube container, such as container 115.

In certain embodiments, the particle size can be between 0.5 mm and 1.5 mm, 0.5 mm and 12 mm, 1 mm and 1.5 mm, 1 mm and 2 mm, 1.5 mm and 3 mm, 3 mm and 6 mm, 6 mm and 9 mm, 6 mm and 12 mm, 9 mm and 12 mm, or any other suitable range. In certain embodiments, the particle size can be 0.5 mm, 1 mm, 1.5 mm, 2 mm, 2.5 mm, 3 mm, 3.5 mm, 4 mm, 4.5 mm, 5 mm, 5.5 mm, 6 mm, 6.5 mm, 7 mm, 7.5 mm, 8 mm, 8.5 mm, 9 mm, 9.5 mm, 10 mm, 10.5 mm, 11 mm, 11.5 mm, 12 mm, or any other suitable size or range extending between any two of the preceding particle sizes. In certain embodiments, one or more of the length, width, height, and diameter of the bone particles can be adjusted to change handling and/or bone growth characteristics.

In certain embodiments, the particles can be spherical, oval, oblong, ellipsoid, polygonal, or any other suitable shape. In certain embodiments, the particles can be fibers, whiskers, chunks, or any other suitable structure.

In certain embodiments, the bone graft material described herein can be used at surgical sites for orthopedic, spine, dental or other any other general surgical applications. For example, in certain embodiments, the bone graft container, such as the container 115, can be used to deliver graft to a disc space. In certain embodiments, the container 115 can be used to deliver bone graft to a disc space before or after implantation of a cage or other interbody device. In some embodiments, the container 115 can be used to deliver bone graft material to a disc space without a cage. In certain embodiments, the bone graft material can be delivered to a tibial plateau or femurs to fill a void after fracture. In certain embodiments, the bone graft material can be delivered to foot or ankle joints or voids for reconstruction. In certain embodiments, one of the ends 122 and 126 can be configured to couple to a cage or a tip for delivery of bone graft material to the surgical location and/or placement of the cage within the disc space.

In certain embodiments, the container 115 can be shaped, dimensioned, or otherwise configured to support cell viability and ease of use by the operating staff and surgeon. With an elongate tube container or cartridge, such as container 115, a much larger outer surface area can be provided in comparison to a traditional storage vial. In certain embodiments, the container 115 of the present application can be elongate and thin to allow for faster thawing time. In certain embodiments, the general outer diameter of the container 115 can be between 2 mm and 12 mm. In certain embodiments, the length of the container 115 can be between 40 mm and 300 mm. In certain embodiments, the container 115 can be sized, shaped, dimensioned, or otherwise configured to hold 1 cc or more of bone graft material, such as cellular matrix. In certain embodiments, the container 115 can hold more than 2 cc of bone graft materially, for example, for dispensing in minimally invasive orthopedic surgeries including spine or for procedures in which less than 2 cc would be burdensome to the user as they would have to open multiple tubes to complete the majority of orthopedic surgeries.

In certain embodiments, the length of the container 115 can be 10 mm, 20 mm, 30 mm, 40 mm, 50 mm, 60 mm, 70 mm, 80 mm, 90 mm, 100 mm, 110 mm, 120 mm, 130 mm, 140 mm, 150 mm, 160 mm, 170 mm, 180 mm, 190 mm, 200 mm, 210 mm, 220 mm, 230 mm, 240 mm, 250 mm, 260 mm, 270 mm, 280 mm, 290 mm, 300 mm, or any other suitable length or range of lengths extending between any two of the preceding lengths.

In certain embodiments, the container 115 can be sized, shaped, dimensioned, or otherwise configured to hold a volume of bone graft of 1 cc, 2 cc, 3 cc, 4 cc, 5 cc, 6 cc, 7 cc, 8 cc, 9 cc, 10 cc, 11 cc, 12 cc, 13 cc, 14 cc, 15 cc, 16 cc, 17 cc, 18 cc, 19 cc, 20 cc, or any other suitable volume or range of volumes extending between any two of the preceding volumes. In certain embodiments, the container 115 can have a volume of 1 cc, 2 cc, 3 cc, 4 cc, 5 cc, 6 cc, 7 cc, 8 cc, 9 cc, 10 cc, 11 cc, 12 cc, 13 cc, 14 cc, 15 cc, 16 cc, 17 cc, 18 cc, 19 cc, 20 cc, or any other suitable volume or range of volumes extending between any two of the preceding volumes.

In some embodiments, the container can have an outer surface area between 1,300 $mm^2$ and 29,000 $mm^2$, 1,300 $mm^2$ and 3,200 $mm^2$, 1,300 $mm^2$ and 5,677 $mm^2$, 1,300 $mm^2$ and 6,450 $mm^2$, 1,300 $mm^2$ and 8,194 $mm^2$, 1,300 $mm^2$ and 9,700 $mm^2$, 2,258 $mm^2$ and 5,677 $mm^2$, 2,258 $mm^2$ and 8,194 $mm^2$, 2,258 $mm^2$ and 9,700 $mm^2$, 2,258 $mm^2$ and 19,355 $mm^2$, 5,677 $mm^2$ and 8,194 $mm^2$, 5,677 $mm^2$ and 9,700 $mm^2$, 8,194 $mm^2$ and 9,700 $mm^2$, 12,900 $mm^2$ and 2,900 $mm^2$, 19,355 $mm^2$ and 25,800 $mm^2$, 19,355 $mm^2$ and 22,710 $mm^2$, 19,355 $mm^2$ and 29,000 $mm^2$, 22,710 $mm^2$ and 25,800 $mm^2$, 22,710 $mm^2$ and 29,000 $mm^2$, or any other suitable range. In certain embodiments, the container 115 can have an outer surface area between 2 $in^2$ and 45 $in^2$, 2 $in^2$ and 5 $in^2$, 2 $in^2$ and 8.8 $in^2$, 2 $in^2$ and 10 $in^2$, 2 $in^2$ and 12.7 $in^2$, 2 $in^2$ and 15 $in^2$, 3.5 $in^2$ and 8.8 $in^2$, 3.5 $in^2$ and 12.7 $in^2$, 3.5 $in^2$ and 15 $in^2$, 3.5 $in^2$ and 30 $in^2$, 8.8 $in^2$ and 12.7 $in^2$, 8.8 $in^2$ and 15 $in^2$, 12.7 $in^2$ and 15 $in^2$, 20 $in^2$ and 45 $in^2$, 30 $in^2$ and 40 $in^2$, 30 $in^2$ and 35.2 $in^2$, 30 $in^2$ and 45 $in^2$, 35.2 $in^2$ and 40 $in^2$, 35.2 $in^2$ and 45 $in^2$, or any other suitable range. In certain embodiments, the outer surface area of the container 115 can be 2 $in^2$, 3 $in^2$, 3.5 $in^2$, 4 $in^2$, 5 $in^2$, 6 $in^2$, 7 $in^2$, 8 $in^2$, 8.8 $in^2$, 9 $in^2$, 10 $in^2$, 11 $in^2$, 12 $in^2$, 12.7 $in^2$, 13 $in^2$, 14 $in^2$, 15 $in^2$, 20 $in^2$, 25 $in^2$, 30 $in^2$, 35 $in^2$, 35.2 $in^2$, 40 $in^2$, 45 $in^2$, or any other suitable surface area or range of surface areas extending between any two of the preceding surface areas. In certain embodiments, the outer surface area of the container 115 can be 1,300 $mm^2$, 2,000 $mm^2$, 2,258 $mm^2$, 2,600 $mm^2$, 3,200 $mm^2$, 3,900 $mm^2$, 4,500 $mm^2$, 5,100 $mm^2$, 5,677 $mm^2$, 5,800 $mm^2$, 6,450 $mm^2$, 7,100 $mm^2$, 7,750 $mm^2$, 8,194 $mm^2$, 8,400 $mm^2$, 9,000 $mm^2$, 9,700 $mm^2$, 12,900 $mm^2$, 16,000 $mm^2$, 19,355 $mm^2$, 22,600 $mm^2$, 22,710 $mm^2$, 25,800 $mm^2$, 29,000 $mm^2$, or any other suitable surface area or range of surface areas extending between any two of the preceding surface areas.

In certain embodiments, the container 115 can have an outer surface area of 5,677 $mm^2$ (8.8 $in^2$) and can have a volume of 5 cc. In certain embodiments, the container 115 can have an outer surface area of 8,194 $mm^2$ (12.7 $in^2$) and can have a volume of 7 cc. In certain embodiments, the container 115 can have an outer surface area of 2,258 $mm^2$ (3.5 $in^2$) and can have a volume of 2 cc. In certain embodiments, the container 115 can have an outer surface area of 22,710 $mm^2$ (35.2 $in^2$) and can have a volume of 20 cc.

In certain embodiments, the wall thickness of the container 115 can range from 0.5 mm to 4 mm. A wall that is thinner than 0.5 mm may crack or burst upon cryopreservation or extruding cellular matrix. A wall thickness greater than 4 mm may prevent the container 115 from fitting in anatomical spaces for graft extrusion. In certain embodiments, the wall thickness of the container 115 can be between 0.5 mm and 2 mm, 0.5 mm and 2.5 mm, 0.5 mm and 3 mm, 0.75 mm and 2 mm, 0.75 mm and 2 mm, 0.75 mm and 2.5 mm, 0.75 mm and 3 mm, 0.75 mm and 4 mm, 1 mm and 2 mm, 1 mm and 3 mm, 1 mm and 4 mm, or any other suitable range. In certain embodiments, the wall thickness of the container 115 can be 0.5 mm, 0.6 mm, 0.75 mm, 1 mm, 1.25 mm, 1.5 mm, 1.75 mm, 2 mm, 2.25 mm, 2.5 mm, 2.75 mm, 3 mm, 3.25 mm, 3.5 mm, 3.75 mm, 4 mm, or any other suitable thickness or range of thicknesses extending between any two of the preceding wall thicknesses.

In certain embodiments, the container 115 can be formed of medical grade biocompatible material approved for short term patient contact. In certain embodiments, the biocompatible material can include one or more polymers. In certain embodiments, the biocompatible material can include polyethylene, polypropylene, ABS, polycarbonate, or any other suitable biocompatible material. In certain embodiments, the container 115 can be formed of materials that are durable and/or maintain mechanical properties after freezing and thawing to resist force imparted on the container by a delivery system. In certain embodiments, the container 115 may be flexible or rigid depending on the application.

In certain embodiments, an inner diameter of the container 115 can be between 0.5 mm and 11.5 mm, 1.5 mm and 8 mm, 1 mm and 4 mm, between 4 mm and 8 mm, between 0.5 mm and 1.5 mm, between 1.5 mm and 3 mm, between 1 mm and 3 mm, between 6 mm and 8 mm, between 8 mm and 10 mm, between 7 mm and 9 mm, or any other suitable range. In certain embodiments, the inner diameter of the container 115 can be 0.5 mm, 1 mm, 1.5 mm, 2 mm, 2.5 mm, 3 mm, 3.5 mm, 4 mm, 4.5 mm, 5 mm, 5.5 mm, 6 mm, 6.5 mm, 7 mm, 7.5 mm, 8 mm, 8.5 mm, 9 mm, 9.5 mm, 10 mm, 10.5 mm, 11 mm, 11.5 mm, or any other suitable diameter or range of diameters extending between any two of the preceding diameters.

In certain embodiments, the container 115 can have a constant inner diameter to allow a plunger of a bone graft delivery device, such as plunger or pushrod 212, to slide freely through the container for graft extrusion. In certain embodiments, the inner diameter may flare out or widen at an end of the container 115. In certain embodiments, the inner diameter may narrow near a distal end of the container so that a plunger of a bone graft delivery device is prevent from extending through the full length of the container 115 or prevented from exit or removal from the container 115.

In certain embodiments, the container 115 can include one or more ridges or recesses. In certain embodiments, the ridges or recesses can provide an increased outer surface area in comparison to a container with a uniform outer diameter.

In certain embodiments, the container 115 is sterilized prior to entering a clean donor processing room for processing and filling of the container 115 with bone graft material. In certain embodiments, the material of the container 115 can be selected for use with means of sterilization such as ebeam, autoclave, EO gas, gamma, or any other suitable means of sterilization.

In certain embodiments, the container 115 can be translucent for graft material visualization in the container 115 to allow assessment of the amount of graft dispensed from the container and/or the amount of graft remaining in the container 115.

In certain embodiments, a cross-section of the container 115 can be circular, square, rectangular, triangular or other suitable shape.

In certain embodiments, a container 115 may be packaged alone or in a kit with multiple containers 115. In certain embodiments, one or more containers can be housed in a sealed pouch for delivery to the operating room. In certain embodiments, the bone graft material, such as cellular matrix, can be loaded in the elongate tubular body 120 at a tissue bank within a clean environment, and then capped and sealed in a pouch to maintain sterility. There may be different methods of maintaining sterility, which are proprietary to each cellular matrix or other bone graft material. The methods may be governed by each manufacture and tissue bank.

In certain embodiments, after removal from the pouch or package, the container 115 can be placed in a saline solution or water for defrosting/thawing. In certain embodiments, the container 115 can be thawed until unfrozen. In certain embodiments, the container 115 is thawed until the bone graft is malleable or pliable. In certain embodiments, the container 115 is thawed until the bone graft is sufficiently malleable or pliable to be capable of dispersion into bone voids. In certain embodiments, the container 115 is thawed unit the bone graft material is sufficiently malleable or pliable to extrude from a bone graft delivery device. In certain embodiments, the container 115 is thawed until the bone graft is at room temperature. In certain embodiments, the container 115 is thawed until the bone graft is at a temperature between 10° C. and 30° C., 15° C. and 25° C., 18° C. and 22° C., or any other suitable range. In certain embodiments, the container 115 is thawed until the bone graft material is at a temperature greater than 10° C., greater than 15° C., greater than 20° C., greater than 25° C., greater than 30° C. or any other suitable range. In certain embodiments, the container 115 is thawed until the bone graft is at a temperature of 10° C., 15° C., 16° C., 17° C., 18° C., 19° C., 20° C., 21° C., 22° C., 23° C., 24° C., 25° C., 30° C., or any other suitable temperature or range of temperatures extending between any two of the preceding temperatures.

In certain embodiments, after thawing, the caps **130*a* and 130*b* on each end of the container 115 may be removed and the elongate tubular body 120 of the container 115 can be attached to a delivery device or a pusher rod, such as push rod 212, may be used to push graft directly out of the elongate tubular body 120 of the container 115. In certain embodiments, a delivery device with a trigger, knob, ratchet, mechanical, pneumatic, electrical, gear, spool design, syringe with extended tip, threaded drive, or any other suitable design may be used to extrude bone graft from the bone graft container 115. In certain embodiments, the container 115** can be attached to such devices for extrusion of the bone graft.

As described in the examples below, the containers of the present application, such as container 115, can be thawed with efficacy in 2 minutes or less. The containers of the present application, such as container 115, can be thawed without hot or warm saline/water. The containers of the present application, such as container 115, can be thawed using room temperature or cool saline/water. In contrast, standard vials containing 5 cc of cellular matrix take on average of 10 minutes to thaw, while standard vials containing 10 cc or 15 cc of cellular matrix taking exponentially longer. The containers of the present application, such as container 115, can reduce time in the operating room to speed up the procedure for the patient and physician.

In certain embodiments, the container 115 can be thawed using water or saline at temperatures below 20°. In certain embodiments, the container 115 can be thawed using water or saline at temperatures between 10° C. and 20° C., 15° C. and 20° C., 20° C. and 25° C., 25° C. and 30° C., 30° C. and 35° C., 35° C. and 40° C., or any other suitable range. In certain embodiments, the container 115 can be thawed using water or saline at temperatures of 10° C., 15° C., 16° C., 17°

C., 18° C., 19° C., 20° C., 21° C., 22° C., 23° C., 24° C., 25° C., 30° C., 35° C., 37° C., 40° C., or any other suitable temperature or range of temperatures extending between any two of the preceding temperatures As described herein, once the bone graft material within the container 115 is thawed, the container 115 can be directly attached to the delivery system/device and a plunger of the delivery system/device, such as plunger or pushrod 212, can be used to deliver bone graft material, such as cellular bone matrix, to the surgical location. Direct attachment of the container 115 can reduce time in loading of a bone graft delivery device as no transfer of material from the storage container to the delivery device is required. Direct attachment of the container 115 to the bone graft delivery system or device can reduce the risk of cross contamination on the operating room table. In certain embodiments, the bone graft material can be sent from a tissue bank and then delivered into the patient without being touched by the operating room staff or instruments for mixing and or delivery.

In certain embodiments, once thawed the container 115 is left with caps 130*a* and 130*b* on to prevent contamination while waiting for use. The caps 130*a* and 130*b* can be removed immediately prior to attachment to the bone graft delivery device or system. In traditional bone graft delivery methods, such as those using vials as shown in FIG. 1, the vials are typically left open once mixed on the operating room table.

When the containers of the present application, such as container 115, are attached to a bone graft delivery device, controlled delivery using the bone graft delivery device is possible. In contrast, in bone graft delivery using a funnel, a user may not be able to determine the amount of graft being delivered.

In certain embodiments, as described herein, one or more caps 130*a* and 130*b* at the ends of the container 115 can prevent the bone graft from spilling. In certain embodiments, the one or more caps 130*a* and 130*b* can include a gasket. The gasket may act as a seal to prevent the bone graft from spilling or leaking. In certain embodiments, the caps 130*a* and 130*b* may be push on, threaded, snap fit, or otherwise releasably engaged to the ends of the elongate tubular body 120 of the container 115. In certain embodiments, one or more caps 130*a* and 130*b* can act as part of the delivery device.

In certain embodiments, the container 115 can include a marker which signals when the cellular matrix is at a proper temperature for use. In certain embodiments, the elongate tubular body 120 can include a marker which signals when the cellular matrix is at a proper temperature for use. In certain embodiments, the marker can be a color indicator or other suitable means for indicating that the bone graft it is ready for use.

In certain embodiments, the container 115 may include a metallic marker or ring to indicate the location of the container 115 using x-ray or fluoroscopy when the container 115 is inserted into the body of the patient for delivery to the surgical site. In certain embodiments, the elongate tubular body 120 can include a metallic marker or ring to indicate the location of the elongate tubular body 120 using x-ray or fluoroscopy when the elongate tubular body 120 is inserted into the body of the patient for delivery to the surgical site In certain embodiments, one or more tips can be attached to the end of the elongate tubular body 120. The tips may provide for distraction or otherwise facilitate access to narrowed disc spaces or bone voids. In certain embodiments, one or more adapters may be attached to the elongate tubular body 120 or form part of the elongate tubular body 120 to facilitate attachment of interbody devices or cages for intervertebral disc spaces.

In certain embodiments, one or more tips may be bi-portal. In certain embodiments, one or more tips may have ridges for decortication, fenestrations, curved angles, prongs, or any other suitable surface features. In certain embodiments, one or more tips can be 3D printed, or CNC machined. In certain embodiments, one or more tips may be made of durable medical polymers, metals, thermoplastics, or any other suitable material. In certain embodiments, one or more tips can be single use sterile packaged disposable or autoclavable for reuse.

In some embodiments, a tip may come pre-assembled on the container 115 or be manufactured on the container 115. In certain embodiments, the shelf life for the cryopreserved container 115 can have a maximum shelf life of 4 years due to the degradation of the packaging, tissue and the container.

As described herein, in certain embodiments, the container 115 is loaded at a tissue bank. In certain embodiments, bone tissue is processed prior to loading in the container 115. In certain embodiments, the tissue is processed in an SAL of 10-3 environment. In certain embodiments, the elongate tubular body 120 of the container 115 is filled at the tissue bank using a funnel, pusher or other customized loading apparatus to couple or mate/abut the elongate tubular body 120. In certain embodiments, the container 115 can be filled with 1 cc, 2 cc, 5 cc, 10 cc or any other suitable amount of bone graft material. In certain embodiments, after the elongate tubular body 115 is filled with bone graft material, the elongate tubular body 120 is capped and/or sealed, for example, with the caps 130*a* and 130*b*. After the container 115 is capped and/or sealed, the filled container 115 can be placed in a pouch or barrier, which can then be sealed. In certain embodiments, the graft cannot be terminally sterilized because the cells will be harmed and cause cell death. After the package is sealed, the package container the container 115 can be frozen to the specifications described herein. In certain embodiments, the package can be maintained in a frozen state until used in the operating room. In certain embodiments, the package can be transferred from a freezer to a box or other shipping container with dry ice for shipping. In certain embodiments, after the container 115 is received at a medical facility for use in an operation, the container 115 can be defrosted in the operating room in the sterile field as described herein. In certain embodiments, the graft may be viable for up to 7 hours after thawing.

Experimental Results

Thaw Time Study

In this study, traditional bone graft vials (Vial), such as the vials shown in FIG. 1, graft tubes in accordance with the present embodiments having a length of 196 mm (7.72 inches) (Elongate Tube 1), and graft tubes in accordance with the present embodiments having a length of 285 mm (11.2 inches) (Elongate Tube 2) were tested to determine the comparative thaw time of each container. Elongate Tubes 1 and 2 are generally similar to the container 115 described herein. 5 Vials were filled with 5 cc of cellular matrix bone graft material. 5 Vials were filled with 7.5 cc of cellular matrix bone graft material. 5 Elongate Tubes 1 were filled with 5 cc of cellular matrix bone graft material. 5 Elongate Tubes 2 were filled with 7.5 cc of cellular matrix bone graft material. Each of the Vials, Elongate Tubes 1, and Elongate Tubes 2 were stored on dry ice at a temperature between −85° and −75 C°. After freezing, each of the Vials, Elongate Tubes 1, and Elongate Tubes 2 were placed into the same temperature saline baths (23° C. and 37° C.). The temperature of the saline baths were chosen due to industry standards.

Once the containers were placed in the bath, they were removed every 30 seconds and the temperature measured with an infrared thermometer. Since the outer container may cool faster than the graft inside, the caps were quickly removed, and the temperature was taken directly on the cellular matrix. Once the cellular matrix temperature reached 20° C., they were considered thawed and the time was recorded. Table 1 indicates the average thaw time for each container in a 23° C. bath and a 37° C. bath.

TABLE 1

| Device | Volume of Bone Graft Material | Wall thickness | Effective Surface Area | Effective Inner Surface Area | Thaw Time in 37° C. Bath (minutes) | Thaw Time in 23° C. Bath (minutes) |
|---|---|---|---|---|---|---|
| Vial: Outer Diameter = 41.15 mm (1.62") Inner Diameter = 36.58 mm (1.44") Length = 35.56 mm (1.40") (however graft only fills 4.76 mm (0.18") of its length) | 5 cc | 2.29 mm (.09") | 1665.9 $mm^2$ (2.58 $in^2$) | 1598.0 $mm^2$ (2.48 $in^2$) | 10 | 15 |
| Elongate Tube 1: Outer Diameter = 9 mm (0.35") Inner Diameter = 6 mm (0.24") Length = 196 mm (7.72") (bone graft fills entire length of tube) Surface Area = 5,677 $mm^2$ | 5 cc | 1.5 mm (.059") | 5598.3 $mm^2$ (8.67 $in^2$) | 3751.1 $mm^2$ (5.81 $in^2$) | 1.5 | 2 |
| Vial: Outer Diameter = 41.15 mm (1.62") Inner Diameter = 36.58 mm (1.44") Length = 35.56 mm (1.40") (however graft only fills 7.14 mm (0.28") of its length) | 7.5 cc | 2.29 mm (.09") | 1973.4 $mm^2$ (3.06 $in^2$) | 1871.46 $mm^2$ (2.90 $in^2$) | 11 | 16.5 |
| Elongate Tube 2: Outer Diameter = 9 mm (0.35") Inner Diameter = 6 mm (0.24") Length = 285 mm (11.2") (bone graft fills entire length of tube) Surface Area = 8,194 $mm^2$ | 7.5 cc | 1.5 mm (.059") | 8114.7 $mm^2$ (12.58 $in^2$) | 5428.7 $mm^2$ (8.41 $in^2$) | 1.5 | 2 |

As shown in Table 1, the thawing time was greatly reduced when using an elongate tube container as described herein. Table 1 also shows a correlation between increased effective surface area, as described further herein, and decreased thaw time. Table 1 further shows a correlation between increased effective inner surface area, as described further herein, and decreased thaw time. It was also noted that even though the infrared thermometer read 20° C. on the outside of the cellular matrix in the Vial, once the cellular matrix was removed from the Vial, the material in the middle was significantly colder. The same results were not noted with the Elongate Tubes 1 and 2.

The effective surface area can be defined as the outer surface area of only the sections of the container housing the bone graft material or the outer surface area of only the sections of the container in which bone graft material is contacting the opposing inside surface. In other words, portions of the container that do not include bone graft material are not considered for the effective surface area measurement. For example, if an elongated tube can house 10 cc of bone graft material, but is only filled with 5 cc such that only half of the volume of the elongate tube is filled with bone graft material, only 50% of the surface area of the elongate tube would be the effective surface area.

Figure 9:
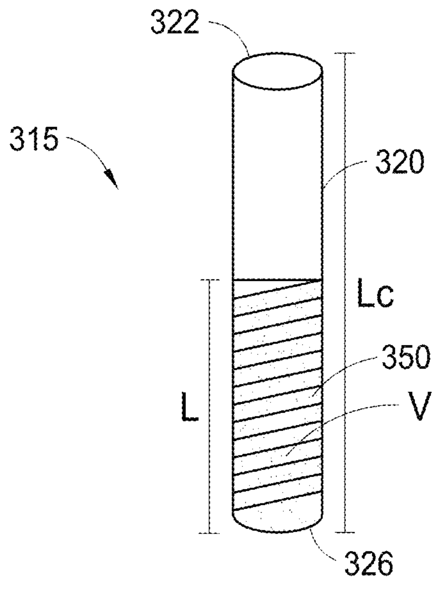
FIG. 9 illustrates a perspective view of another embodiment of a container for storing bone graft material.
Figure 10:
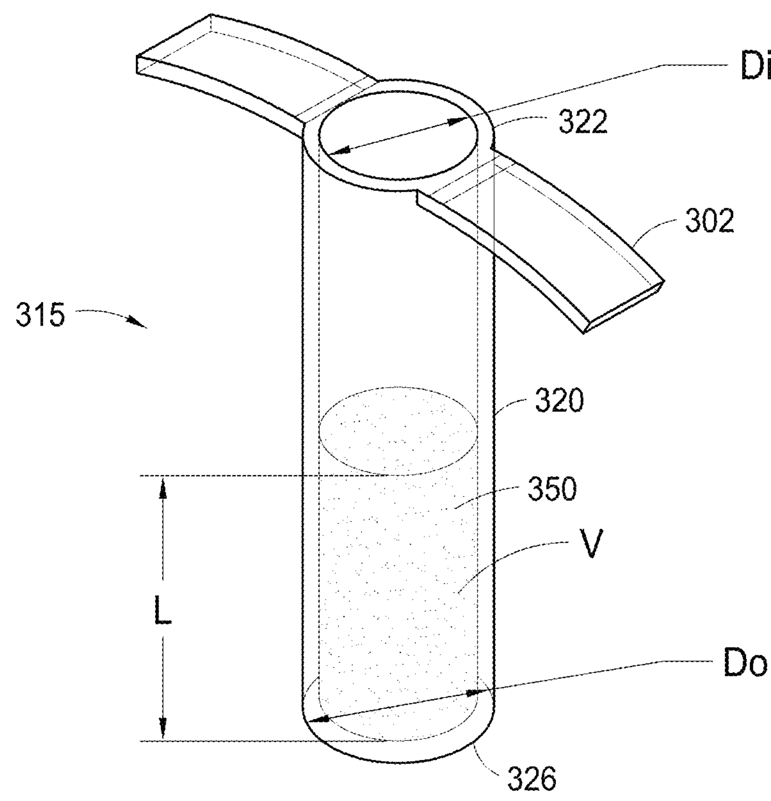
FIG. 10 illustrates a perspective view of the container of FIG. 9 and a handle.

FIG. 9 depicts an embodiment of a container 315 having an elongate tubular body 320, an end 322, and an end 326. The container 315 can include any of the same or similar features and functions as the container 115. As shown in FIG. 9, the container 315 is partially filled with a bone graft material 350. FIG. 10 depicts the container 315 partially filled with bone graft material 350 coupled to a handle 322.

As shown in FIGS. 9 and 10, the bone graft 350 inside the container 315 can have a volume V having a length L, which represents a distance between a first end of a volume V of bone graft material 350 within the container 315 to a second end of the volume V of bone graft material 350 within the container 315. The container 315 can have a length $L_c$, an outer diameter $D_o$ and an inner diameter $D_i$.

For a cylindrical or generally cylindrical container, such as containers 115 and 315, having an outer diameter $D_o$ and an inner diameter $D_i$, with a volume of bone graft inside the container V having a length of bone graft inside the container L, in which the volume of bone graft contacts only one end of the container, effective surface area (SA) and effective surface area to volume ratio (SA/V) are calculated as:

$$SA = \pi D_o L + \frac{\pi D_i^2}{4} \quad \text{(Equation 1)}$$

$$V = \text{cellular bone matrix volume} \quad \text{(Equation 2)}$$

$$\frac{SA}{V} = \frac{4\pi D_o L + \pi Di^2}{4V}$$

For a cylindrical or generally cylindrical container, such as containers 115 and 315, having an outer diameter $D_o$ and an inner diameter $D_i$, with a volume of bone graft inside the container V having a length of bone graft inside the container L, in which bone graft material contacts both ends of the container (a container that is full of bone graft material), effective surface area (SA) and effective surface area to volume ratio (SA/V) are calculated as:

$$SA = \pi D_o L + \frac{\pi D_i^2}{2} \quad \text{(Equation 3)}$$

$$V = \text{cellular bone matrix volume} \quad \text{(Equation 4)}$$

$$\frac{SA}{V} = \frac{2\pi D_o L + \pi Di^2}{2V}$$

An example calculation for the Elongate Tube 1 in Table 1 filled with 5 cc (5000 $mm^3$) of cellular bone matrix is as follows:

$$SA = \pi D_o L + \frac{\pi Di^2}{2} = \pi(9.00\text{ mm})(196\text{ mm}) + \frac{\pi(6.0\text{ mm})^2}{2}$$

-continued $$SA = 5598.3\ \text{mm}^2$$

$$V = \text{Bone graft volume} = 5000\ \text{mm}^3$$

$$\frac{SA}{V} = \frac{5598.3\ \text{mm}^3}{5000\ \text{mm}^3} = 1.12$$

The Vial used in the test in Table 1 has an outer diameter $D_o$ of 41.15 mm, an inner diameter $D_i$ of 36.58 mm, a length of cellular bone matrix inside the container L of 4.76 mm. With a volume of cellular bone matrix inside the container V of 5 cc (5000 mm$^3$), the effective surface area to volume ratio is calculated as:

$$SA = \pi D_o L + \frac{\pi Di^2}{4} = \pi(41.15\ \text{mm})(4.76\ \text{mm}) + \frac{\pi(36.58\ \text{mm})^2}{4}$$

$$SA = 1665.9\ \text{mm}^2$$

$$V = \text{Bone graft volume} = 5000\ \text{mm}^3$$

$$\frac{SA}{V} = \frac{1665.9\ \text{mm}^2}{5000\ \text{mm}^3} = 0.33$$

As shown herein, the Vial of Table 1 has a lower effective surface area to volume ratio than the Elongate Tube 1 of Table 1. It took over six times as long for the cellular bone matrix within the Vial to thaw when placed in 37° saline water in comparison to the cellular bone matrix material within the Elongate Tube 1.

As shown in Table 1, the Elongate Tube 2 has the same inner diameter and outer diameter as the Elongate Tube 1, but has a longer length in comparison to the Elongate Tube 1. If filled with the same amount of bone graft material, the Elongate Tube 2 would have the same length of bone graft material as the Elongate Tube 1, and consequently, the same effective surface area (unless the Elongate Tube 1 is completely filled such that the bone graft material contacts both ends of the Elongate Tube 1).

In conventional practice, it is common to only partially fill a vial, such as the Vial of Table 1, often less than halfway, which can decrease effective surface area and increases thaw time. For example, as shown in Table 1, 5 cc of bone graft filled to a length L of 4.76 mm within the Vial having a length $L_c$ of 35.56 mm was found to have a thaw time of 10 minutes in a 37° C. bath and a thaw time of 15 minutes in a 23° C. bath. Such a distribution of bone graft material may not be optimal for thawing evenly and quickly.

In some embodiments, an elongate tubular container, such as the container 115 or the container 315, is completely filled, substantially filled, or more than 50% filled with bone graft material. In certain embodiments, the elongate tubular container is completely filled with bone graft material to allow for maximum bone graft distribution. Completely filling an elongate tubular container, such as container 115 or 315, can provide a larger effective surface area, which can in turn decreases thaw time for an optimal amount of bone graft material. As shown in Table 1, the Vial, the Elongate Tube 1, and the Elongate Tube 2 can each hold 5 cc of bone graft material. However, the effective surface areas of the Elongate Tube 1 and the Elongate Tube 2 are greater than the effective surface area of the Vial.

Table 1 also illustrates that, when filled with 7.5 cc of bone graft material, the Elongate Tube 2 has an effective surface area of 8114.73 mm$^2$, and the Vial has an effective surface area of 1973.4 mm$^2$. The effective surface area to volume ratio of the Elongate Tube 2 is 1.08:1 and the effective surface area to volume ratio of the vial is 0.26:1 when the effective surface area is measured in square millimeters and the volume is measured in cubic millimeters.

In certain embodiments, applicants have found that for a cellular bone matrix bone graft material, an advantageous ratio of an effective surface area of a container to a volume of cellular bone matrix bone graft material in the container can be greater than greater than 0.4:1, greater than 0.5:1, greater than 0.6:1, greater than 0.7:1, greater than 0.8:1, greater than 0.9:1, greater than 1.0:1, greater than 1.1:1, greater than 1.2:1, greater than 1.3:1, greater than 1.4:1, greater than 1.5:1, or any other suitable range when the effective surface area is measured in square millimeters and the volume is measured in cubic millimeters. In certain embodiments, a ratio between 0.4:1 and 1.5:1, between 0.7:1 and 1.2:1, or any other suitable range may provide for faster thaw times when the effective surface area is measured in square millimeters and the volume is measured in cubic millimeters.

In certain embodiments, the elongate tubular containers described herein, such as the container 115 or the container 315, can have an effective surface area between 1,800 mm$^2$ and 12,000 mm$^2$, 2,500 mm$^2$ and 11,000 mm$^2$, 3,500 mm$^2$ and 10,500 mm$^2$, 4,500 mm$^2$ and 10,000 mm$^2$, 5,000 mm$^2$ and 95,000 mm$^2$, or any other suitable range. In certain embodiments, an elongate tubular container, such as the container 115 or the container 315, can have an effective surface area between 5,000 mm$^2$ and 9,000 mm$^2$.

The effective inner surface area can be defined as the inner surface area of only the sections of the container housing the bone graft material or the inner surface area of only the sections of the container in which bone graft material is contacting the inner surface. In other words, portions of the container that do not include bone graft material are not considered for the effective inner surface area measurement. For example, if an elongated tube can house 10 cc of bone graft material, but is only filled with 5 cc such that only half of the volume of the elongate tube is filled with bone graft material, only 50% of the inner surface area of the elongate tube would be the effective inner surface area.

For a cylindrical or generally cylindrical container, such as containers 115 and 315, having an inner diameter $D_i$, with a volume of bone graft inside the container V having a length of bone graft inside the container L, in which the volume of bone graft contacts only one end of the container, effective inner surface area ($SA_i$) and effective inner surface area to volume ratio ($SA_i/V$) are calculated as:

$$SA_i = \pi D_i L + \frac{\pi D_i^2}{4} \quad \text{(Equation 5)}$$

$$V = \text{cellular bone matrix volume} \quad \text{(Equation 6)}$$

$$\frac{SA_i}{V} = \frac{4\pi D_i L + \pi D_i^2}{4V}$$

For a cylindrical or generally cylindrical container, such as containers 115 and 315, having an outer diameter $D_o$ and an inner diameter $D_i$, with a volume of bone graft inside the container V having a length of bone graft inside the container L, in which bone graft material contacts both ends of the container (a container that is full of bone graft material), effective inner surface area ($SA_i$) and effective inner surface area to volume ratio ($SA_i/V$) are calculated as:

$$SA_i = \pi D_i L + \frac{\pi D_i^2}{2} \quad \text{(Equation 7)}$$

$$V = \text{cellular bone matrix volume} \quad \text{(Equation 8)}$$

$$\frac{SA_i}{V} = \frac{2\pi D_i L + \pi D_i^2}{2V}$$

An example calculation for the Elongate Tube 1 in Table 1 filled with 5 cc (5000 $mm^3$) of cellular bone matrix is as follows:

$$SA_i = \pi D_i L + \frac{\pi D_i^2}{2} = \pi(6.00\text{ mm})(196\text{ mm}) + \frac{\pi(6.0\text{ mm})^2}{2}$$

$$SA_i = 3751.1\text{ mm}^2$$

$$V = \text{Bone graft volume} = 5000\text{ mm}^3$$

$$\frac{SA_i}{V} = \frac{3751.1\text{ mm}^2}{5000\text{ mm}^3} = 0.75$$

The Vial used in the test in Table 1 has an outer diameter $D_o$ of 41.15 mm, an inner diameter $D_i$ of 36.58 mm, a length of cellular bone matrix inside the container L of 4.76 mm. With a volume of cellular bone matrix inside the container V of 5 cc (5000 $mm^3$), the effective inner surface area to volume ratio is calculated as:

$$SA_i = \pi D_i L + \frac{\pi D_i^2}{4} = \pi(36.58\text{ mm})(4.76\text{ mm}) + \frac{\pi(36.58\text{ mm})^2}{4}$$

$$SA_i = 1598.0\text{ mm}^2$$

$$V = \text{Bone graft volume} = 5000\text{ mm}^3$$

$$\frac{SA_i}{V} = \frac{1598.0\text{ mm}^2}{5000\text{ mm}^3} = 0.32$$

As shown herein, the Vial of Table 1 has a lower effective inner surface area to volume ratio than the Elongate Tube 1 of Table 1. It took over six times as long for the cellular bone matrix within the Vial to thaw when placed in 37° saline water in comparison to the cellular bone matrix material within the Elongate Tube 1.

As shown in Table 1, the Elongate Tube 2 has the same inner diameter and outer diameter as the Elongate Tube 1, but has a longer length in comparison to the Elongate Tube 1. If filled with the same amount of bone graft material, the Elongate Tube 2 would have the same length of bone graft material as the Elongate Tube 1, and consequently, the same effective inner surface area (unless the Elongate Tube 1 is completely filled such that the bone graft material contacts both ends of the Elongate Tube 1).

In conventional practice, it is common to only partially fill a vial, such as the Vial of Table 1, often less than halfway, which can decrease effective inner surface area and increases thaw time. For example, as shown in Table 1, 5 cc of bone graft filled to a length L of 4.76 mm within the Vial having a length $L_c$ of 35.56 mm was found to have a thaw time of 10 minutes in a 37° C. bath and a thaw time of 15 minutes in a 23° C. bath. Such a distribution of bone graft material may not be optimal for thawing evenly and quickly.

In some embodiments, an elongate tubular container, such as the container 115 or the container 315, is completely filled, substantially filled, or more than 50% filled with bone graft material. In certain embodiments, the elongate tubular container is completely filled with bone graft material to allow for maximum bone graft distribution. Completely filling an elongate tubular container, such as container 115 or 315, can provide a larger effective inner surface area, which can in turn decreases thaw time for an optimal amount of bone graft material. As shown in Table 1, the Vial, the Elongate Tube 1, and the Elongate Tube 2 can each hold 5 cc of bone graft material. However, the effective inner surface areas of the Elongate Tube 1 and the Elongate Tube 2 are greater than the effective inner surface area of the Vial.

Table 1 also illustrates that, when filled with 7.5 cc of bone graft material, the Elongate Tube 2 has an effective inner surface area of 5428.7 $mm^2$, and the Vial has an effective inner surface area of 1871.46 $mm^2$. The effective inner surface area to volume ratio of the Elongate Tube 2 is 0.72:1 and the effective inner surface area to volume ratio of the vial is 0.25:1 when the effective inner surface area is measured in square millimeters and the volume is measured in cubic millimeters.

In certain embodiments, applicants have found that for a cellular bone matrix bone graft material, an advantageous ratio of an effective inner surface area of a container to a volume of cellular bone matrix bone graft material in the container can be greater than greater than 0.4:1, greater than 0.5:1, greater than 0.6:1, greater than 0.7:1, greater than 0.8:1, greater than 0.9:1, greater than 1.0:1, greater than 1.1:1, greater than 1.2:1, greater than 1.3:1, greater than 1.4:1, greater than 1.5:1, or any other suitable range when the effective inner surface area is measured in square millimeters and the volume is measured in cubic millimeters. In certain embodiments, a ratio between 0.4:1 and 1.5:1, between 0.5 and 1.0, between 0.6 and 0.9, between 0.65 and 0.75, between 0.7 and 0.8, between 0.7:1 and 1.2:1, or any other suitable range may provide for faster thaw times when the effective inner surface area is measured in square millimeters and the volume is measured in cubic millimeters.

In certain embodiments, the elongate tubular containers described herein, such as the container 115 or the container 315, can have an effective inner surface area between 2,060 $mm^2$ and 19,157 $mm^2$, between 3,500 $mm^2$ and 6,000 $mm^2$, between 3,500 $mm^2$ and 10,000 $mm^2$, between 5,000 $mm^2$ and 10,000 $mm^2$, between 10,000 $mm^2$ and 20,000 $mm^2$, between 15,000 $mm^2$ and 20,000 $mm^2$, or any other suitable range.

Post Cryopreservation Wall Thickness Strength Testing—Burst

In this study, graft tubes in accordance with the embodiments described herein, such as containers 115 and 315, with varying wall thickness were tested. Three tubes at each wall thickness diameter were tested before and after cryopreservation. Each tube had a length of 1.96 mm (7.72") and a diameter of 9 mm (0.35"). Each tube was filled with cellular matrix, cryopreserved, and then stored at a constant −75° C. to −85° C. for 7 days. The tubes were then thawed in a 37° C. saline bath and then put through a burst test to determine if they could withstand at least 30 lbf. This number was determined based on previous tests of the force it takes to dispense industry standard cellular matrix material using a bone graft delivery system.

To begin the test, a cap was screwed onto one end of the tube and a plunger inserted into the opposite end. The plunger must extend at least 1.5" out of the end of the tube so that it can be attached to a force gauge. A clamp was then attached to the end of the tube with the cap and the tube was pressed at increasing forces into the force gauge. This was continued until either the force gauge reached 30 lbf or the tube burst. Significant signs of degradation or any cracks were considered a failure. Table 2(a) shows the results of performing the burst test on each tube thickness before cryopreservation. Table 2(b) shows the results of performing the burst test on each tube thickness after cryopreservation.

TABLE 2(a)

| Sample | Material | Wall Thickness (mm) | Pass Burst Test? |
|---|---|---|---|
| Tube 1 | Polypropylene | 2.0 | Yes |
| Tube 2 | Polypropylene | 1.5 | Yes |
| Tube 3 | Polypropylene | 1.0 | Yes |
| Tube 4 | Polypropylene | .75 | Yes |
| Tube 5 | Polypropylene | .6 | Yes |
| Tube 6 | Polypropylene | .4 | Yes |

TABLE 2(b)

| Sample | Material | Wall Thickness (mm) | Pass Burst Test? |
|---|---|---|---|
| Tube 1 | Polypropylene | 2.0 | Yes |
| Tube 2 | Polypropylene | 1.5 | Yes |
| Tube 3 | Polypropylene | 1.0 | Yes |
| Tube 4 | Polypropylene | .75 | Yes |
| Tube 5 | Polypropylene | .6 | No |
| Tube 6 | Polypropylene | .4 | No |

As shown from the results in Tables 2(a) and 2(*b*), the cryopreservation did have an effect on the tubes integrity. The tubes seemed to get more brittle and demonstrated that at thinner diameters, could not withstand necessary forced to perform their function.

Examples of tubes having failed the burst test are provided in FIGS. 3A-D.

Post Cryopreservation Wall Thickness Strength Testing—Bend

In this study, graft tubes with varying wall thickness were tested. Three tubes at each wall thickness were tested before and after cryopreservation. Each tube had a length of 196 mm (7.72") and a diameter of 9 mm (0.35"). Each tube was filled with cellular matrix, cryopreserved, and then stored at a constant −75° C. to −85° C. for 7 days. The tubes were then thawed in a 37° C. saline bath and then the cellular matrix was extruded. They were then put through a bend test to determine if they could withstand common bend forces that may occur during surgery.

For each tube, one end was securely placed within a vice grip and bent in a series of directions. Each tube was bent 45° to the operators left, right, forward and backward with a momentary pause in between each bend. This was repeated twice for each tube. Significant signs of degradation or any cracks would be considered a failure. Table 3(a) shows the results of performing the bend test on each tube thickness before cryopreservation. Table 3(b) shows the results of performing the bend test on each tube thickness after cryopreservation.

TABLE 3(a)

| Sample | Material | Wall Thickness (mm) | Pass Bend Test? |
|---|---|---|---|
| Tube 1 | Polypropylene | 2.0 | Yes |
| Tube 2 | Polypropylene | 1.5 | Yes |
| Tube 3 | Polypropylene | 1.0 | Yes |
| Tube 4 | Polypropylene | .75 | Yes |
| Tube 5 | Polypropylene | .6 | Yes |
| Tube 6 | Polypropylene | .4 | No |

TABLE 3(b)

| Sample | Material | Wall Thickness (mm) | Pass Bend Test? |
|---|---|---|---|
| Tube 1 | Polypropylene | 2.0 | Yes |
| Tube 2 | Polypropylene | 1.5 | Yes |
| Tube 3 | Polypropylene | 1.0 | Yes |
| Tube 4 | Polypropylene | .75 | Yes |
| Tube 5 | Polypropylene | .6 | No |
| Tube 6 | Polypropylene | .4 | No |

Figure 4B:
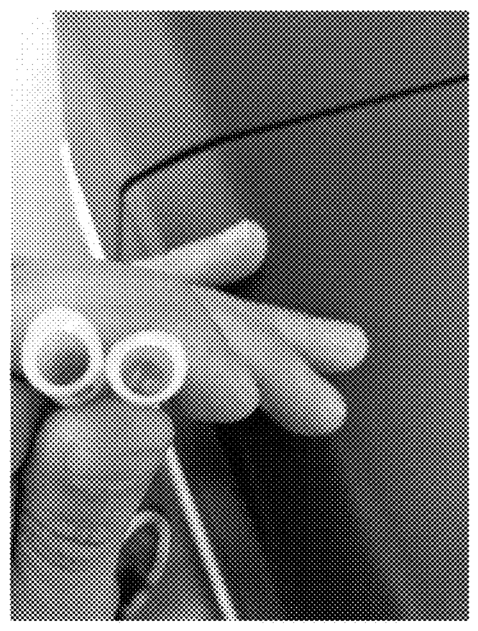
FIG. 4B illustrates an example of a container having failed a bend test.
Figure 4C:
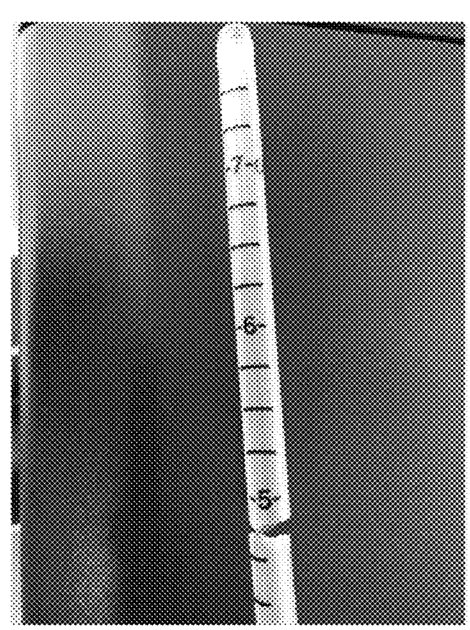
FIG. 4C illustrates an example of a container having failed a bend test.
Figure 4A:
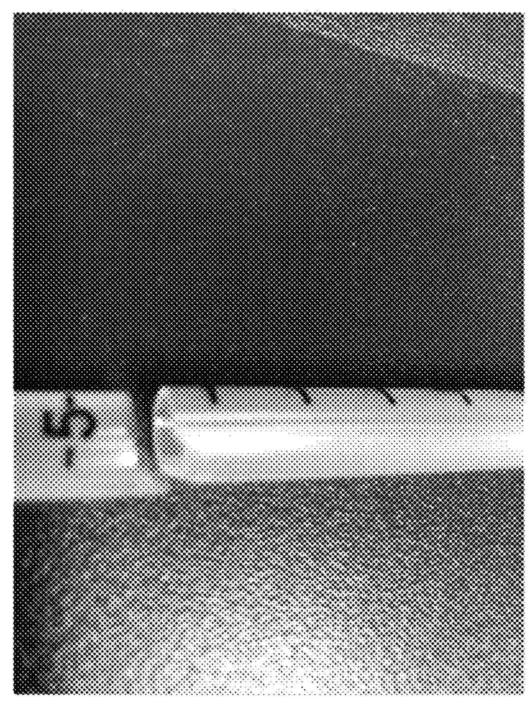
FIG. 4A illustrates an example of a container having failed a bend test.

As shown from the results, the cryopreservation did have an effect on the tubes integrity. The tubes appeared to become more brittle. The experiment demonstrated that at thinner thicknesses (0.6 mm and 0.4 mm), the tubes could not withstand the forces imparted by the bend test. Examples of tubes having failed the bend test are provided in FIGS. 4A-C.

The above tests demonstrate that length, diameter, and/or wall thickness can determine the effectiveness of a container for cellular matrix. Cryopreservation and temperatures of −75° C. to −85° C. can have strong effects on the integrity of a material used for storage of bone graft material. When developing a tube to hold the bone graft material, such as cellular matrix, it can be desirable to have a wall thickness that can withstand these negative changes. Furthermore, the shape of a container for storing bone graft material as described in the embodiments herein can improve the thaw time of the cellular matrix. Thaw time is a key feature of cellular matrix products because decreased thaw time can reduce the time of handling the bone matrix container in the operating room after removal from cryopreservation. This can reduce the likelihood of contamination and simplify bone graft delivery for the operating room staff.

In certain embodiments, the material of the container can be selected to optimize the rate of thawing of the bone graft material. For example, in certain embodiments, the container can be formed of a material or composite having a thermal conductivity coefficient k lower than 0.6. For example, in some embodiments, the material or composite can be a plastic or polymer. Example materials are shown in Table 4 below:

TABLE 4

| Material | Thermal Conductivity @25° C. (W/m · K) |
|---|---|
| Acrylic | 0.20 |
| Polycarbonate | 0.19 |
| Polypropylene | 0.1-0.22 |
| Polyethylene, Low Density | 0.33 |
| Polyethylene, High Density | 0.42-.051 |

In certain embodiments, materials such as glass and steel can have higher thermal conductivity coefficients which may allow faster transfer of heat. In certain embodiments, glass and steel may have higher thermal conductivity coefficients that cause heating to occur too rapidly or the temperature of the bone graft material to become too high such that cells die and the properties of cellular bone matrix degrade. In certain embodiments, glass containers may be dangerous for surgical applications, such as minimally invasive applications, due to brittleness and the possibility of fracture.

Various modifications to the implementations described in this disclosure may be readily apparent to those skilled in the art, and the generic principles defined herein may be applied to other implementations without departing from the spirit or scope of this disclosure. Thus, the disclosure is not intended to be limited to the implementations shown herein, but is to be accorded the widest scope consistent with the principles and features disclosed herein. Various combinations and subcombinations of the various features described herein are possible.

While this invention has been particularly shown and described with reference to embodiments thereof, it will be understood by those skilled in the art that various changes in form and details may be made therein without departing from the scope of the invention. For all of the embodiments described above, the steps of the methods need not be performed sequentially.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, 0.1 degree, or otherwise.

It will be apparent to those skilled in the art that various modifications and variations can be made in the present invention without departing from the scope or spirit of the invention. Thus, it is intended that the present invention cover modifications and variations of this invention.

What is claimed is:

1. A method for delivering bone graft material to a surgical location comprising:

placing a container within a 23° C. bath, the container housing a bone graft material in a frozen state, wherein the bone graft material comprises cellular matrix, wherein the container comprises an elongate tubular body having a first opening on a first end and a second opening on a second end, the elongate tubular body having an outer diameter of 9 mm, an inner diameter of 6 mm, a wall thickness of 1.5 mm; and either a first length of 196 mm, a first effective outer surface area of 5598.3 $mm^2$ and a first effective inner surface area of 3751.1 $mm^2$, or a second length of 285 mm, a second effective outer surface area of 8114.7 $mm^2$, and a second effective inner surface area of 5428.7 $mm^2$; wherein the first effective outer surface area or the second effective outer surface area of the container is an outer surface area of only sections of the container housing the bone graft material or an outer surface of only sections of container in which the bone graft material contacts an opposing inside surface of the container, wherein the first effective inner surface area or the second effective inner surface area of the container is an inner surface area of only sections of the container housing the bone graft material or an inner surface area of only sections of the container in which the bone graft material contacts an inner surface of the container, wherein placing the container within the bath thaws the bone graft material within 2 minutes;

removing the container from the bath;

coupling the elongate tubular body to a body of a bone graft delivery device while the bone graft material is positioned within the elongate tubular body; and delivering bone graft material through the elongate tubular body to a surgical location using the bone graft delivery device.

2. The method of claim 1, wherein removing the container from the bath comprises removing the container from the bath after a temperature of the bone graft material within the container is above 20° C.

3. The method of claim 1, wherein removing the container from the bath comprises removing the container from the bath after a temperature of the bone graft material within the container is between 1° C. and 42° C.

4. The method of claim 1, wherein the container comprises a first plug, cap, or seal covering the first opening and a second plug, cap, or seal covering the second opening.

5. The method of claim 4, further comprising removing the first plug, cap, or seal from the elongate tubular body prior to coupling the elongate tubular body to the bone graft delivery device.

6. The method of claim 1, wherein the bone graft delivery device comprises a plunger, wherein delivering bone graft material comprises advancing the plunger through the elongate tubular body.

7. The method of claim 6, wherein the bone graft delivery device comprises a handle configured to removably couple to the elongate tubular body, wherein the handle comprises a channel configured to align with the first opening of the elongate tubular body and receive the plunger therethrough.

8. The method of claim 1, wherein delivering the bone graft material is performed without rinsing the bone graft material after the bone graft material is thawed.

9. A container for storing and delivering bone graft material, the container comprising:

an elongate tubular body comprising:
- a first opening on a first end;
- a second opening on a second end;
- an outer diameter of 9 mm;
- an inner diameter of 6 mm;
- a wall thickness of 1.5 mm; and
- either a first length of 196 mm, a first effective outer surface area of 5598.3 $mm^2$, and a first effective inner surface area of 3751.1 $mm^2$, or a second length of 285 mm, a second effective outer surface area of 8114.7 $mm^2$, and a second effective inner surface area of 5428.7 $mm^2$, a first cap, plug, or seal covering the first opening;

a second cap, plug, or seal covering the second opening; and a bone graft material comprising cellular matrix within the elongate tubular body;

wherein:
- the elongate tubular body is configured to allow the cellular matrix to thaw from a frozen state within 2 minutes when the elongate tubular body is placed in a 23° C. bath;
- the first effective outer surface area or the second effective outer surface area of the container is an outer surface area of only sections of the container housing the bone graft material or an outer surface of only sections of container in which the bone graft material contacts an opposing inside surface of the container; and
- the first effective inner surface area or the second effective inner surface area of the container is an inner surface area of only sections of the container housing the bone graft material or an inner surface area of only sections of the container in which the bone graft material contacts an inner surface of the container.

10. The container of claim 9, wherein the elongate tubular body is configured to allow the cellular matrix to thaw from a frozen state to a temperature above 20° C. within 2 minutes when the elongate tubular body is placed in a 23° C. bath.

11. The container of claim 9, wherein the elongate tubular body is configured to withstand at least 30 lbf in a burst test.

12. The container of claim 9, wherein the elongate tubular body is configured to withstand bending to 45° in a forward direction, a rearward direction, a leftward direction, and a rightward direction in a bend test.

13. The container of claim 9, wherein the elongate tubular body is configured to allow the cellular matrix to thaw from a frozen state to a temperature suitable for delivery and introduction into the body when the elongate tubular body is placed in a 23° C. bath.

14. A bone graft delivery system comprising:

the container of claim 9; and a plunger configured to be advanced through the first opening of the elongate tubular body to advance the bone graft material out of the second opening of the elongate tubular body.

15. The bone graft delivery system of claim 14, further comprising a handle configured to be removably coupled to the elongate tubular body, wherein the handle comprises a channel configured to align with the first opening of the elongate tubular body and receive the plunger therethrough.

16. A method for thawing a bone graft material, comprising:

receiving a container comprising an elongate tubular body and housing a bone graft material in a frozen state, wherein the elongate tubular body comprises an outer diameter of 9 mm, an inner diameter of 6 mm, a wall thickness of 1.5 mm, and either a first length of 196 mm, a first effective outer surface area of 5598.3 $mm^2$, and a first effective inner surface area of 3751.1 $mm^2$, or a second length of 285 mm, a second effective outer surface area of 8114.7 $mm^2$, and a second effective inner surface area of 5428.7 $mm^2$, and placing the container within a bath at a temperature of 23° C. to thaw the bone graft material within 2 minutes;

wherein:

the first effective outer surface area or the second effective outer surface area of the container is an outer surface area of only sections of the container housing the bone graft material or an outer surface of only sections of container in which the bone graft material contacts an opposing inside surface of the container; and the first effective inner surface area or the second effective inner surface area of the container is an inner surface area of only sections of the container housing the bone graft material or an inner surface area of only sections of the container in which the bone graft material contacts an inner surface of the container.

17. The method of claim 16, further comprising removing the container from the bath after a temperature of the bone graft material within the container is above 20° C.

* * * * *